US 6,548,652 B2

(12) United States Patent
Lukhtanov et al.

(10) Patent No.: US 6,548,652 B2
(45) Date of Patent: Apr. 15, 2003

(54) ATTACHMENT OF OLIGONUCLEOTIDES TO SOLID SUPPORTS THROUGH SCHIFF BASE TYPE LINKAGES FOR CAPTURE AND DETECTION OF NUCLEIC ACIDS

(75) Inventors: Eugeny Alexander Lukhtanov, Bothell, WA (US); Mikhail A. Podyminogin, Lake Forest Park, WA (US); Joel Hedgpeth, San Francisco, CA (US)

(73) Assignee: Epoch Biosciences, Inc., Bothell, WA (US)

( * ) Notice: Subject to any disclaimer, the term of this patent is extended or adjusted under 35 U.S.C. 154(b) by 0 days.

(21) Appl. No.: 09/780,954

(22) Filed: Feb. 9, 2001

(65) Prior Publication Data

US 2002/0081591 A1 Jun. 27, 2002

Related U.S. Application Data

(62) Division of application No. 09/364,320, filed on Jul. 29, 1999, now Pat. No. 6,339,147.

(51) Int. Cl.[7] .................. C07H 19/00; C07H 21/00; C07H 21/02; C07H 21/04; C12Q 1/68
(52) U.S. Cl. .............. 536/23.1; 536/24.3; 536/24.5; 536/25.3; 536/25.33; 536/26.6; 435/6
(58) Field of Search ............... 435/6; 536/23.1, 536/24.3, 24.5, 25.3, 25.33, 26.6

(56) References Cited

U.S. PATENT DOCUMENTS

| 5,210,015 A | 5/1993 | Gelfand et al. ............ 435/6 |
| 5,492,806 A | 2/1996 | Drmanac et al. ........... 435/5 |
| 5,512,667 A | 4/1996 | Reed et al. .............. 536/24.31 |
| 5,514,785 A | 5/1996 | Van Ness ............... 536/22.1 |
| 5,525,464 A | 6/1996 | Drmanac et al. ........... 435/6 |
| 5,556,752 A | 9/1996 | Lockhart et al. ........... 435/6 |
| 5,801,155 A | 9/1998 | Kutyavin et al. .......... 514/44 |
| 5,849,482 A | 12/1998 | Meyer, Jr. et al. ......... 435/6 |
| 5,880,270 A | 3/1999 | Berminger et al. | |

FOREIGN PATENT DOCUMENTS

| EP | 0 152 886 A2 | 8/1985 | |
| WO | 92/10588 | 6/1992 | ........ C12Q/1/68 |
| WO | 96/17957 | 6/1996 | ........ C12Q/1/68 |

OTHER PUBLICATIONS

Kremsky et al. Nucleic Acids Research, vol. 15, No: 7, pp. 2891–2909, 1987.*
Wolf et al. Nucleic Acids Research, vol. 15, No: 7, pp. 2911–2926, 1987.*
Guo et al., "Direct fluorescence analysis of genetic polymorphisms by hybridization with oligonucleotide arrays on glass supports," *Nucleic Acids Research*, vol. 22, No. 24, pp. 5456–5465, Oxford University Press, (Oct. 24, 1994).
Katritzky et al., "New Synthesis of SASRIN™ Resin, " *Tetrahedron Letters*, vol. 38, No. 45, pp. 7849–7850, Elsevier Science Ltd., Printed in Great Britain, (1997).

(List continued on next page.)

*Primary Examiner*—Jezia Riley
(74) *Attorney, Agent, or Firm*—Townsend and Townsend and Crew LLP

(57) ABSTRACT

Derivatized oligonucleotides (ODNs) are coupled to a solid support in improved yield resulting in a high density of coupled oligonucleotide per surface unit of the support, through a Schiff base type bond formed between an $NH_2$ group attached either to the solid support or to the ODN and an aromatic aldehyde attached to the other of the solid support and the ODN. The preferred solid support-ODN conjugate is formed between semicarbazide groups attached to a glass surface and an aromatic aldehyde attached at either 3', or 5' end of an ODN or to an intermediate nucleotide of the ODN.

17 Claims, 6 Drawing Sheets

OTHER PUBLICATIONS

Routledge et al., "New Fluoride–Labile Linkers for Solid–Phase Organic Synthesis," *Tetrahedron Letters*, vol. 38, No. 47, pp. 8287–8290, Elsevier Science Ltd., Printed in Great Britain, (1997).
Ramsay, Nat. Biotech., 16:40–44 (1998).
Nat. Genet., 21(1): 1–60 (1999).
Rogers et al., Anal. Biochem., 266:23–30 (1990).
Highsmith et al., J. Biotechniques 12: 418–23 (1992).
Ghosh et al., Nuc. Acid Res., 15:5353–5372 (1987).
Kremsky et al., Nuc. Acid Res., 15:2891–2909 (1987).
Tsarev et al., (Biorg. Khim., 16:765–79 (1990)). See English language abstract on page 779.
Guo et al., (Nuc. Acid Res., 22:5456–5465 (1994).
Joos et al., Anal. Biochem., 247:96–101 (1997).
Beattie et al., Mol. Biotech., 4:213–225 (1995).
Hayatsu, Biochem., 15:2677–2682 (1976).
Lipshutz et al., Nat. Genet., 21:20–24 (1999).
Weiler et al., Nucl. Acids Res., 25: 2792–9 (1997).
Nielsen, Curr Opin Biotechnol. 10:71–5 (1999).
Koch et al., Tetrahedron Let., 36:6933–6936 (1995).
Van Ness et al., Nucleic Acids Res. 19: 3345–3350 (1991).
Gago, Methods, 14: 277–92 (1998).
Ausubel et al., Edit., in Current Protocols in Molecular Biology, 1.5.1–1.5.10 (1990) John Wiley & Sons, New York.
Cheng et al, Nucl. Acids Res. 24: 380–385 (1996).
Mitchell et al., Anal. Biochem., 178: 239–42 (1989).
O'Shannessy et al., in Anal. Biochem., 191: 1–8 (1990).
Wittwer et al., Biotechniques 22: 130–138 (1997).
Luktanov et al., Bioconjug. Chem., 7: 564–567 (1996).
Bernstein et al., J. Am. Chem, Soc., 73: 906–912 (1951).
Lehmann et al., Carbohydr. Res., 169: 53–68 (1987).
Whitaker et al., Analytical Biochemistry, 207: 267–279 (1992).
Maskos et al., Nucleic Acids Research, 21: 2267–2268 (1993).
Holland et al., Proc. Natl. Acad. Sci. USA, 88: 7276–7280 (1991).

* cited by examiner

FIG. 4.

ATTACHMENT OF OLIGONUCLEOTIDES TO SOLID SUPPORTS THROUGH SCHIFF BASE TYPE LINKAGES FOR CAPTURE AND DETECTION OF NUCLEIC ACIDS

This application is a divisional of and claims the benefit of U.S. Ser. No. 09/364,320, filed Jul. 29, 1999, now U.S. Pat. No. 6,339,147 the disclosure of which is incorporated by reference.

FIELD OF THE INVENTION

The present invention generally relates to the chemistry of the attachment of oligonucleotides to solid supports. More particularly the present invention relates to linking oligonucleotides to solid supports through a Schiff base type covalent linkage for capture and detection of single- and double stranded DNA and RNA targets.

BACKGROUND OF THE INVENTION

The detection and quantification of very small quantifies of nucleic acids plays an important role in the biological, forensic and medical sciences. Typically nucleic acids in samples are detected by hybridization to a complementary oligonucleotide containing more than 8 contiguous nucleotides. To provide a signal proportional to the target-oligonucleotide hybrid, typically either the target or the second probe contains a signal generating label, such as a radioactive-, fluorescent-, chemiluminescent-moiety or an enzyme (such as horseradish peroxidase) that through its catalytic activity yields a detectable product. The prior art is well developed in this regard and numerous methods are available for the detection and quantification of signal in the nucleic acid field.

Following the hybridization of the capturing and labeled oligonucleotide to the target nucleic acid it is necessary to separate the signal generating duplex from unreacted target and labeled oligonucleotide. This can usually be accomplished because either the target, or more typically the capturing oligonucleotide has been immobilized on a solid support thereby allowing the isolation of the hybrid free from unhybridized molecules. In a "sandwich assay" variation, an oligonucleotide is immobilized to a solid support and is used to capture a target. The captured target is detected by hybridization with a second labeled oligonucleotide, that has a different sequence than the capturing oligonucleotide.

Numerous types of solid supports suitable for immobilizing oligonucleotides are known in the art. These include nylon, nitrocelluose, activated agarose, diazotized cellulose, latex particles, plastic, polystyrene, glass and polymer coated surfaces. These solid supports are used in many formats such as membranes, microtiter plates, beads, probes, dipsticks etc. A wide variety of chemical procedures are known to covalently link oligonucleotides directly or through a linker to these solid supports. Of particular interest as background to the present invention is the use of glass and nylon surfaces in the preparation of DNA microarrays which have been described in recent years (Ramsay, Nat. Biotechnol., 16: 40–4 (1998)). The journal Nature Genetics has published a special supplement describing the utility and limitations of microarrays (Nat.Genet., 21(1): 1–60 (1999)).

Typically the use of any solid support requires the presence of a nucleophilic group to react with an oligonucleotide that must contain a "reactive group" capable of reacting with the nucleophilic group. Alternatively, a "reactive group" is present or is introduced into the solid support to react with a nucleophile present in or attached to the oligonucleotide. Suitable nucleophilic groups or moieties include hydroxyl, sulfhydryl, amino and activated carboxyl groups, while the groups capable of reacting with these and other nucleophiles (reactive groups) include dichlorotriazinyl, alkylepoxy, maleimido, bromoacetyl goups and others. Chemical procedures to introduce the nucleophilic or the reactive groups on to solid support are known in the art, they include procedures to activate nylon (U.S. Pat. No. 5,514,785), glass (Rodgers et al., Anal. Biochem., 23–30 (1999)), agarose (Highsmith et al., J., Biotechniques 12: 418–23 (1992)) and polystyrene (Gosh et al., Nuc. Acid Res., 15: 5353–5372 (1987)). Dependent on the presence of either a reactive or nucleophilic groups on the solid support and oligonucleotide, coupling can either be performed directly or with bifunctional reagents. Bifunctional and coupling reagents are well known in the art and many are available from commercial sources.

Of special interest as background to the present invention is the procedure described by Kremsky et al. (Nuc.Acid Res., 15: 2891–2909 (1987)) for the preparation of a 16-mer oligonucleotide containing a 6 carbon carboxylic acid linker on the 5'-end. This product was synthesized using the appropriate phosphoramidites on a standard synthesizer. The acid was then reacted with 3-amino-1,2-propanediol in the presence of 1-(3-dimethylaminopropyl)-3-ethylcarbodiimide to yield a stable diol. The diol was oxidized to the aliphatic aldehyde stage that was subsequently reacted with hydrazide latex beads to form Schiff base linkages that were reduced with sodium cyanoborohydride. The authors indicated that the oligonucleotide diol was a stable intermediate but that the aldehyde should be prepared immediately before coupling to the latex bead to minimize undesirable reaction of the aldehyde with the oligonucleotide bases.

Another article of special interest as background to the present invention is by Tsarev et al. (Biorg.Khim., 16: 765–79 (1990)) that describes coupling of an aromatic aldehyde to the 5' phosphate of an oligonucleotide through alkylation. The product was used to probe the RNA polymerase promoter complex.

Typically, glass surfaces are activated by the introduction of amino-, sulfhydryl-, carboxyl- or epoxy-groups to the glass using the appropriate siloxane reagent. Specifically, immobilization of oligonucleotide arrays on glass supports has been described: by Guo et al., Nuc. Acid Res., 22: 5456–5465 (1994) using 1,4-phenylene diisothiocyanate; by Joos et al., Anal. Biochem., 247: 96–101 (1997) using succinic anhydride and carbodiimide coupling; and by Beatti, et al., Mol. Biotech., 4: 213–225 (1995) using 3-glycidoxypropyltrimethoxysilane.

The rapid specific reaction of cytidine in single stranded DNA with semicarbazide moiety containing reagent, in the presence of bisulfite, has also been described (Hayatsu, Biochem., 15: 2677–2682 (1976)).

Procedures which utilize arrays of immobilized oligonucleotides, such as sequencing by hybridization and array-based analysis of gene expression are known in the art. In these procedures, an ordered array of oligonucleotides of different known sequences is used as a platform for hybridization to one or more test polynucleotides, nucleic acids or nucleic acid populations. Determination of the oligonucleotides which are hybridized and alignment of their known sequences allows reconstruction of the sequence of the test polynucleotide. See, for example, U.S. Pat. Nos. 5,492,806; 5,525,464; 5,556,752; PCT Publications WO 92/10588, WO 96/17957 and the scientific publications by Ramsay, Nat. Biotechnol., 16: 40–4 (1998) and by Lipshutz et al., Nat. Genet., 21: 20–24 (1999)).

Hybridization based DNA screening on peptide nucleic acid (PNA) oligomer arrays has been described (Weiler et al, Nucl. Acids Res., 25: 2792–9 (1997). PNAs and PNA/DNA chimeras are also well described.((Nielsen, Curr Opin Biotechnol. 10: 71–5 (1999); Koch et al., Tetrahedron Let., 36: 6933–6936 (1995)).

However, many of the current immobilization methods suffer from one or more of a number of disadvantages. Some of these are, complex and expensive reaction schemes with low oligonucleotide loading yields, reactive unstable intermediates prone to side reactions and unfavorable hybridization kinetics of the immobilized oligonucleotide. The efficient immobilization of oligonucleotides on glass surface in arrays in a high-through put mode requires a) simple reliable reactions giving reproducible loading for different batches, b) stable reaction intermediates, c) arrays with high loading and fast hybridization rates, d) high temperature stability, e) low cost, f) specific attachment at either the 5'- or 3'-end or at an internal nucleotide and g) low background.

The present invention represents a significant step in the direction of meeting or approaching several of these objectives.

SUMMARY OF THE INVENTION

In accordance with the present invention a Schiff base type covalent linkage is formed between a group containing an $NH_2$ moiety and an aromatic aldehyde or ketone to covalently link an oligonucleotide (ODN) to a solid support. The Schiff base type linkage is formed between the solid support and either the 3', or 5' end of the ODN, or between the solid support and one or more intermediate nucleotides in the ODN. Alternatively the Schiff base type linkage is located in a combination of these sites. In this regard it should be understood that the Schiff base type covalent linkage may be situated not directly on the solid support or the ODN but on linking groups (linkers) which are themselves covalently attached to the solid support and to the ODN, respectively. Thus, either the solid support or the ODN or both may include a linking group that includes the —$NH_2$ or aromatic aldehyde group which forms the Schiff base type covalent bond to join the ODN to the solid support.

In accordance with one aspect and preferred mode or embodiment of the invention the Schiff base type covalent bond is formed between a semicarbazide group or moiety of the formula R'—NH—CO—NH—$NH_2$, and the aromatic aldehyde moiety of the formula R"—Q—CHO, preferably a benzaldehyde moiety, where the group R' designates either the solid support or the ODN residue including any linker group attached to the solid support or ODN, and where the R" designates the other of said solid support or ODN residues including any linker group attached to them. The symbol Q in this formula designates an aromatic ring or a heteroaromatic ring which may have up to three heteroatoms independently selected from N, O and S, and where the aromatic or heteroaromatic ring may itself be substituted with alkyl, alkoxy or halogen groups where the alkyl or alkoxy group preferably has 1 to 6 carbons. The linkage formed between the solid support and the ODN is thus depicted by the formula

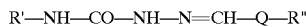

where the symbols have the meaning provided above.

In accordance with still another aspect and preferred mode or embodiment of the invention the semicarbazide moiety is attached to a glass surface, and the benzaldehyde moiety is attached with a linker to the 3', or to the 5' end of the ODN, or to one or more nucleotides situated internally in the ODN. The synthetic methodologies to prepare the semicarbazide modified solid support surface and the aromatic aldehyde coupled ODNs comprise still further aspects of the present invention.

Advantages of the solid support ODN conjugates linked together with the above-summarized Schiff base type linkages including an aromatic aldehyde or ketone, and particularly with semicarbazone linkages, include (a) their ability to be formed below pH 7, (b) stability of the Schiff base-with-aromatic-aldehyde bonds and particularly of the semicarbazone-formed-with-an-aromatic-aldehyde bonds, (c) ability to attach a high percentage (typically more than 60%, and preferably about 90%, even more preferably 95% or more) of the ODN to the semicarbazide moiety containing solid support, d) specific attachment at either the 5'- or 3'-end or at an internal nucleotide, and (e) obtaining high coupling densities (preferably of about $10^4$ oligonucleotides/$\mu m^2$ and most preferably about $10^5$ oligonucleotides/$\mu m^2$) on unit surface of the solid support. These advantages are to be contrasted with the prior art procedures, see for example [Kremsky et al. (Nuc.Acid Res., 15: 2891–2909 (1987))] where an aliphatic aldehyde attached to the ODN is coupled with a hydrazide-containing solid support to form a hydrazone that is unstable and must be reduced to provide a stable solid support-ODN conjugate.

Another aspect of the present invention is a general method of attaching oligonucleotides to a solid support at a specified end, or other position specified by the placement of the aldehyde or semicarbazide moiety to generate probes for specific polynucleotide sequences. In this case the oligonucleotide is usually attached at the 3'- or 5'-end so that the extent of the oligonucleotide sequence is available for hybridization to a target polynucleotide in, for example, a mixture of polynucleotides of different sequence. The polynucleotides can be labeled with fluorescent, radioactive, chemical or other detectors known in the art. The oligonucleotides may also contain moieties that enhance duplex stabilization, such as minor groove binders, as is described in U.S. Pat. No. 5,801,155, incorporated herein by reference, or modified bases such as pyrazolopyrimidines (as is described in PCT US99/07492 incorporated herein by reference. The stringency and specificity of the hybridization can be adjusted by any of several means known in the art, such as temperature, salt concentration and composition and/or chaotropic agents as is described in the publication by Van Ness et al., Nucleic Acids Res. 19: 5143–51 (1991) incorporated herein by reference, such that only perfectly base-paired duplexes form and the unhybridized polynucleotides removed by washing and the hybridized polynucleotides identified by their attached label(s).

In still another aspect of the present invention, the oligonucleotide attached to a solid support as described above, can be used to hybridize to a polynucleotide, present in a mixture of polynucleotides, under specific conditions, and the unhybridized polynucleotides removed as described above. A second oligonucleotide containing a specific distinguishable label (e.g. radioactive isotope, fluorophore or chemically identifiable compound) can be used to hybridize to a region of the target polynucleotide separate from that hybridized to the first oligonucleotide fixed to the solid support. The second oligonucleotide can contain compounds that enhanced specific duplex formation, such as minor groove binders (U.S. Pat. No. 5,801,155) or modified bases such as pyrazolopyrimidines (PCT Publication US99/

07492) and intercalators (as described for example by Gago, Methods, 14: 277–92 (1998) incorporated herein by reference.). After washing to remove unhybridized oligonucleotide(s), the presence of the sequence to which the second oligonucleotide hybridized can be determined by measuring the presence of the label on the second oligonucleotide. Multiple oligonucleotides can be attached to the solid support and multiple oligonucleotides each with a specific label can be used as the second oligonucleotide.

In yet another aspect of this invention, the second oligonucleotide and the first (attached) oligonucleotide can be chosen so that if they hybridize adjacent to one another on the complementary labeled target polynucleotide, they can be ligated to one another, thereby forming a longer oligonucleotide with an inherently higher melting point (Tm). In this case the washing conditions can by adjusted so that no oligonucleotide that is unligated can remain in a duplex with the target polynucleotide. The use of DNA and RNA ligases is well known to those skilled in the art (see for example Lee, Biologicals, 24: 197–199 (1996) incorporated herein by reference).

In a further aspect of this invention, the second labeled oligonucleotide and the first (attached) oligonucleotide can be chosen so that if they hybridize adjacent to one another on the complementary target polynucleotide, they can be ligated to one another, only if they are a perfect match.

In a still further aspect of the invention, oligonucleotides can be constructed with the aldehyde (or semicarbazide) incorporated in one of the described configurations so that the 3'-terminus of the oligonucleotide can be extended by a polymerase. The oligonucleotides so constructed can be used as single primers to generate cDNA or as one member of a primer pair to generate amplicons in the polymerase chain reaction in reactions well described in the literature (see for example Ausubel et al. Edit., in Current Protocols in Molecular Biology, 1:5.5.1–5.5.10 (1990) John Wiley & Sons, New York, incorporated herein by reference). In each of these cases the polynucleotide to be analyzed serves as the template for polynucleotide synthesis primed by aldehyde or semicarbazide containing oligonucleotides which are at least partially complementary to the polynucleotide. The product double-stranded polynucleotide can be attached to a solid support containing the semicarbazide (or aldehyde) moiety. This support containing the double stranded molecules can be used to capture and detect or purify molecules that bind to the sequences present in the attached polynucleotides. Alternatively, the attached double-stranded polynucleotides can be denatured (for example by heating or treating with reagents like NaOH) and the single strand polynucleotides attached via the Shiff's base covalent linkage remain attached to the solid support and the complementary strand (s) are removed. The single strands remaining on the solid support can now be used as hybridization targets or as targets for other molecules that bind to single stranded polynucleotides.

In a variation of this method, the double stranded polynucleotides can be denatured (i.e. the duplexes converted to single strands) prior to attachment to the solid support via the Schiff's base formation.

In yet another aspect of this invention, an oligonucleotide can be constructed so that attachment to the solid support via the Schiff's base is achieved so that the oligonucleotide is free to hybridize to a target polynucleotide so that it can be digested by an enzyme that acts only on double strand polynucleotides. The attached oligonucleotide is constructed to contain a fluorophore and a quencher that blocks the fluorescence of the fluorophore, positioned in such a way that when the oligonucleotide forms a duplex with its complement in a mixture of polynucleotides, it can be cleaved by the enzyme to separate the quencher and the fluororphore, generating a fluorescent signal at the position on the solid support where the oligonucleotide was attached. Although many different double strand specific enzymes would be useful in this method, a specific case would be the use of DNA polymerases in the polymerase chain reaction. In this case the oligonucleotide attached to the solid support contains a quencher at its 5'-end and a fluorophore coupled elsewhere, usually at the 3'-end. A second oligonucleotide complementary to the target polynucleotide in a region serves as a primer 5' from the attached oligonucleotide (containing the quencher and fluorophore). As the polymerase extends the primer, it digests the attached oligonucleotide from the 5'-end releasing the base(s) to which the quencher is attached and the polynucleotide-attached oligonucleotide duplex dissociates, leaving the portion of the attached oligonucleotide containing the fluorophore attached to the solid support. Subjecting the resulting oligonucleotide to the appropriate light generates a fluorescent signal at the position of the attachment of the oligonucleotide. FIG. 6 shows where in addition to the fluorophore and quencher, a minor groove binder is also incorporated into the oligonucleotide conjugate. Reagents and methods for carrying out polymerase chain reactions on solid supports are well known to those skilled in the art, see for example Cheng et al., Nucl. Acids Res. 24: 380–385 (1996).

Another aspect of the present invention is a general method for the isolation of single stranded DNA in a process where an aldehyde-labeled primer is used and an amplicon is immobilized on a semicarbazide containing solid support. Denaturation of the amplicon and separation yield single stranded DNA in solution and on the solid support, which could be used individually for many applications known in the art. This is an improvement and further development of the procedure described by Mitchell et al., Anal. Biochem., 178: 239–42 (1989), where single-stranded DNA is "affinity generated" following a polymerase chain reaction using a biotinylated primer, followed by streptavidin-solid support separation.

In accordance with yet another aspect of the present invention, non-specific adsorption of the negatively charged nucleic acids to the semicarbazide or other amine-modified glass surface can be largely eliminated by converting the unreacted $NH_2$ groups (preferably semicarbazide —R'—NH—CO—NH—$NH_2$ groups) into a moiety containing an anion. This is accomplished by reacting the ODN attached to the solid support with a reagent that introduces an anionic group, for example by reacting the solid support with 4-formyl-1,3-benzenedisulfonic acid. In addition, unreacted silanol functions on the solid support, preferably glass surface are end-capped with a hydrophobic siloxane to increase stability of the immobilized oligonucleotides.

Although this is not usually necessary, the semicarbazone linkages formed with the aromatic aldehyde moiety and linking the oligonucleotide with the solid support can be reduced to provide still stable solid-support-ODN conjugates.

In accordance with a still further aspect of the present invention an ODN containing cytidine is immobilized on a solid support containing semicarbazide groups by bisulfite catalyzed covalent attachment through the cytidine nucleotides of the ODN.

It should be understood that generally speaking for the purpose of this invention an oligonucleotide comprises a plurality of nucleotide units, a 3' end and a 5' end. The nucleotide may contain one or modified bases other than the normal purine and pyrimidine bases. In addition an oligonucleotide may include peptide oligonucleotides (PNAs) or PNA/DNA chimeras. The oligonucleotide may also contain groups that can influence its binding to a complementary strand, e.g. minor group binders or intercalators, or groups necessary for its detection e.g. fluorophores and quenchers The present invention is primarily used at present for the capture and detection of nucleic acids using oligonucleotides attached to glass surfaces with the Schiff base type, (preferably semicarbazone) bonds, and more particularly for the capture and detection of PCR generated nucleic acid sequence in array format, although the use of the invention is not limited in this manner. Generally speaking the oligonucleotides immobilized on solid support in accordance with the present invention exhibit superior direct capture ability for complementary oligonucleotide, DNA and RNA sequences.

BRIEF DESCRIPTION OF THE DRAWINGS

FIG. 4 is the depiction of a hybridization of macroarray consisting of six ODN probes to eight different 30-mer ODN targets, the sequences of which are disclosed in Table 1, wherein each oligonucleotide is spotted in triplicate giving an array of 3×6 spots and wherein the target sequences 1 and 8 correspond to X and Y copy of the amelogenin gene and wherein all other target sequences contain nucleotide substitutions at positions indicated in bold in Table 1 and wherein match or mismatch of the base pairs formed between each probe and the target are indicated at the bottom of each ODN triplicate.

DESCRIPTION OF THE PREFERRED EMBODIMENTS

Derivatized Supports

Figure 1:
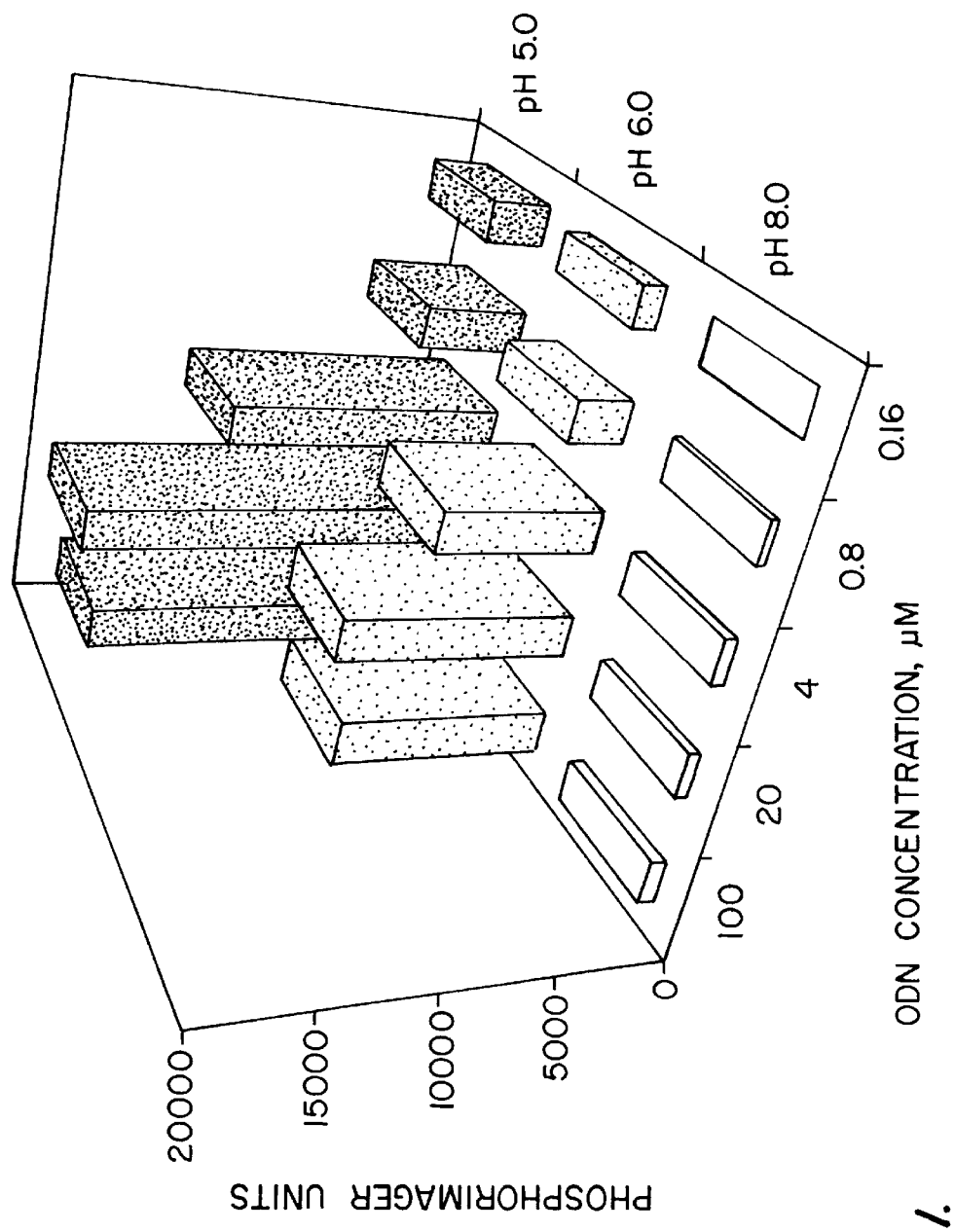
FIG. 1 is a graph showing in three dimensions the optimization of oligonucleotide attachment via semicarbazone bonds to a glass surface as a function of concentration of the oligonucleotide and pH of the media.

As is noted in the Summary, in accordance with the present invention one of the solid support or the oligonucleotide (ODN) contains a nucleophilic amino group while the other contains an aromatic or heteroaromatic aldehyde or ketone capable of reacting with the nucleophilic amino group to form a Schiff base-type covalent linkage that attaches the ODN to the solid support, in a reasonably fast, high yield reaction resulting in high concentrations of the ODN per unit surface of the solid support, bound thereto by a stable covalent bond. In order to have these properties the nucleophilic amino group preferably and ideally has a pKa less than 7.0 In the preferred embodiments the nucleophilic amino ($NH_2$) group is covalently linked to the solid support while the aromatic aldehyde or ketone (preferably aldehyde) is linked to the ODN.

Thus, the solid supports used in the preferred embodiments of the invention contain the nucleophilic $NH_2$ group, as a primary amine (R'—$NH_2$), or as a hydrazinyl, (R'—NH—$NH_2$), aminooxy (O—$NH_2$), or semicarbazido (R'—NH—CO—NH—$NH_2$) group. R' simply denotes the rest of the solid support, including a possible linking group or linker). Most preferably the solid support in accordance with the present invention includes a semicarbazido group attached to the matrix of the solid support with a linker containing more than one atom and less than 30 atoms. These amino ($NH_2$) group containing moieties can be introduced on to the solid support or surface by methods known in the art.

Among the several types of solid supports available in the art glass is most preferred. In accordance with this preferred embodiment of the invention the glass surface contains the nucleophilic amino ($NH_2$) group, which, as noted above, may be primary amino, hydrazinyl, acylhydrazinyl, aminooxy, or a semicarbazido group, linked to the glass surface with a linker containing more than one atom and less than 30 atoms. Most preferably a semicarbazido group is linked to the glass surface with the linker. The semicarbazido group has a pKa less than 7.0. The semicarbazido and other amino ($NH_2$) groups can be introduced on to the glass surface by methods known in the art, involving a reaction with an appropriate trialkyloxysilane. For the most preferred embodiments of the invention the semicarbazido group is introduced to the glass surface with a semicarbazide containing trialkyloxysilane, as is shown in Reaction Scheme 1.

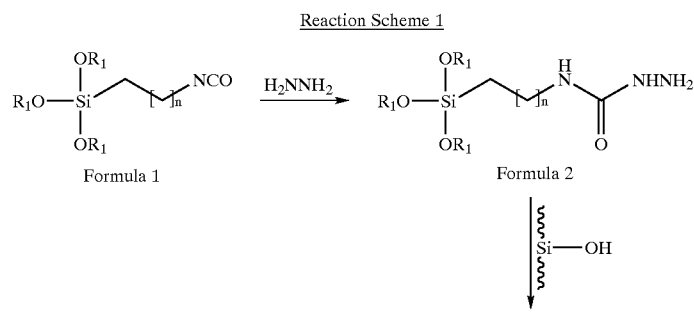

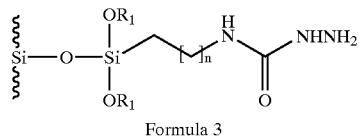

Formula 3

In Reaction Scheme 1 $R_1$ represents an alkyl group of 1 to 10 carbons, although one of more of the $R_1$ groups can also be hydrogen or aryl. In the presently most preferred embodiment $R_1$ is ethyl. n is an integer, preferably having the values of 0 to 30, even more preferably 0 to 10. Thus, in accordance with this scheme a trialkoxy siloxane compound (Formula 1) having an isocyano group attached by an alkyl chain is reacted with hydrazine to provide a trialkoxysilane including a semicarbazide (Formula 2), which is thereafter reacted with the glass surface to provide a glass surface (solid support) having a semicarbazide groups attached through the linker $(CH_2)_n$. (Formula 3). A detailed description of the conditions of these reactions is provided in the experimental section of this application for patent.

Derivatized Oligonucleotides

In the preferred embodiments of the invention an aromatic or heteroaromatic aldehyde is covalently linked to the oligonucleotide (ODN), so as to enable the ODN to react with the nucleophilic $NH_2$ (preferably semicarbazide) groups linked to the solid support.

Prior to the current invention methods for the introduction of aldehyde groups into oligonucleotides were complicated and required post oligo-synthesis periodate oxidation of a diol precursor, as described by O'Shannessy et al., in Anal. Biochem., 191: 1–8 (1990)). It is a novel aspect or feature of the present invention to provide a phosphoramidite reagent that includes a protected aromatic aldehyde and which can be used for the introduction of the aldehyde group into an ODN during standard automated oligonucleotide synthesis. In the most preferred embodiments the aromatic aldehyde group or moiety is the "benzaldehyde" moiety having a linker designated "$R_x$" attached to the phenyl ring, as illustrated in Reaction Scheme 2 by Formula 4.

In Formula 4 the symbol $R_x$ represents a chain of atoms, which may include a ring, and which may have the overall length of 2 to 150 atoms. $R_x$ may contain atoms selected from C, H, N, O and S and in addition may contain one or more of —NH—, —O—, —NH—C(=O)—, —C=(O)—NH—, —NH—C(=O)—NH—, —NH—C(=S)—NH—, —S—, OP(O)(O$^-$)O or —S—S— groups. Synthetic methods to construct $R_x$ are known in the art and are described, for example, in U.S. Pat. No. 5,849,482 in connection with the description of synthesizing linker arms. The specification of U.S. Pat. No. 5,849,482 is expressly incorporated herein by reference. It should be understood that instead of the aromatic aldehyde of Formula 4, an aromatic ketone (such as acetophenone) could also be used, although the use of the aldehyde is preferred.

In accordance with Reaction Scheme 2 the aromatic aldehyde (or ketone) of Formula 4 is protected in the aldehyde group by formation of a diacetal, cyclic acetal or dialkanoate derivative of Formula 5. In Formula 5 $R_2$ represents an alkyl group of 1 to 6 carbons, an acyl group of one to 6 carbons, or the two $R_2$ groups together form a carbocyclic ring of 2–4 carbons (as in a cyclic acetal, for example in a cyclic acetal formed with ethylene glycol). The protected aldehyde of Formula 5 is then converted into a phosphoramidite reagent of Formula 6, as is shown in the reaction scheme. Detailed experimental conditions for this conversion are described for an example in the experimental section. The phosphoramidite reagent of Formula 6 is then used later to introduce the protected aldehyde into an oligonucleotide (as described below.

Reaction Scheme 2

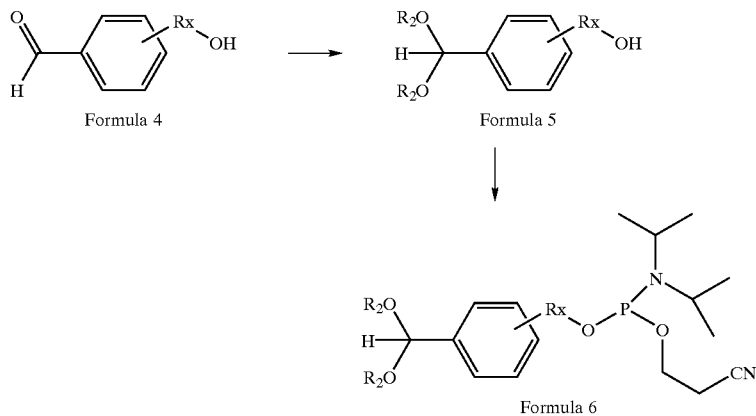

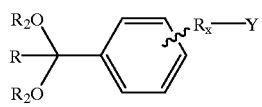

Formula 7

Instead of the phosphoramidite reagent of Formula 6 the protected aromatic aldehyde can also be attached to a primary or secondary amino group that is itself attached to the 5' or to the 3' end of an ODN, or to a primary or secondary amino group that is attached to an internal nucleotide in the ODN. Amino-tailed ODNs can be prepared in accordance with the state-of-the-art, and are described for example in U.S. Pat. No. 5,512,667 the specification of which is incorporated herein by reference. A reagent that is suitable for attaching a protected aromatic aldehyde to said amino groups at either tail end of the ODN or to one or more internal nucleotides is shown in Formula 7. In Formula 7 $R_2$ and $R_x$ are defined as in connection with Formula 5. R is preferably hydrogen, but can also be lower alkyl. Y is a reactive group (capable of reacting with a nucleophilic amine), such as a carbonate, isocyanate, isothiocyanate, mono or di-substituted pyridine, aziridine, CO—X, $SO_2$—X (X is halogen), monochlorotriazine, dichlorotriazine, hydroxysulfosuccinimide ester, hydroxysuccinimide ester, azidonitrophenyl or azido group. As example it is noted that an appropriately acitivated 3-($\alpha,\alpha$-dimethoxytolu-4-yl) propionic acid derivative can be coupled to 5-(3-aminopropyl)uridine nucleotide incorporated in the ODN as an internal base. Instead of an aromatic aldehyde an aromatic ketone (where R is lower alkyl) can also be used.

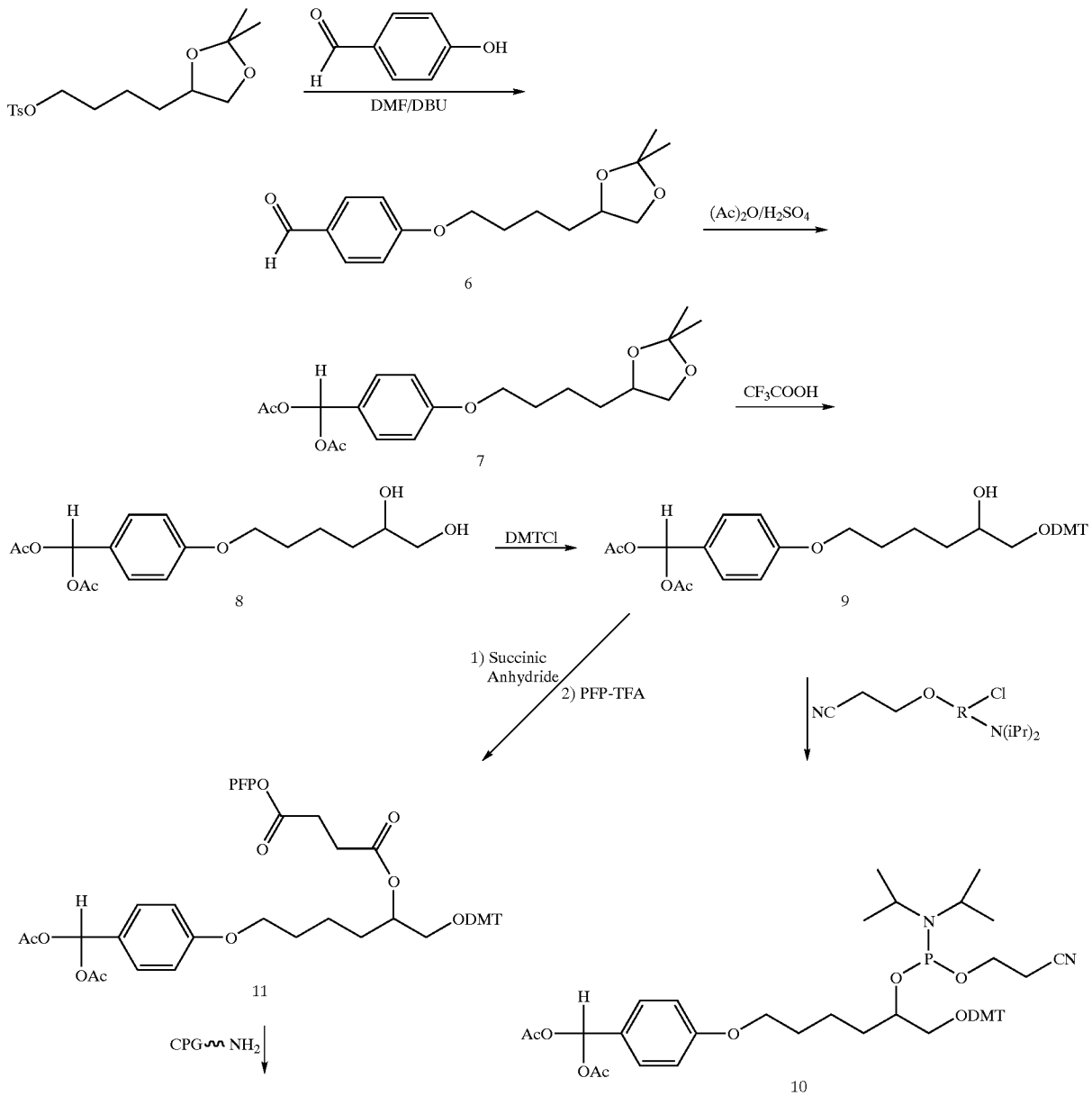

Reaction Scheme 3

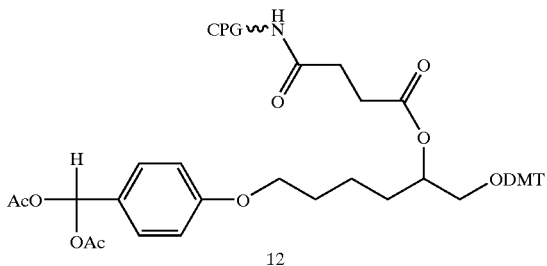

12

Reaction Scheme 3 discloses an actual example for the synthesis of a controlled pore glass reagent 12 suitable for the synthesis of 3'-aromatic-aldehyde-tailed oligonucleotides. In this regard it should be understood that in the present description the numbers given to actual compounds are to be distinguished from numbers given to general formulas. Thus, the compound designated "6" in Reaction Scheme 3 is to be distinguished from Formula 6 in Reaction Scheme 2. A detailed description of the exemplary reaction conditions leading to the protected aldehyde function attached to a controlled pore glass support designated 12 in the scheme, is provided in the experimental section. The CPG support 12 includes a dimethoxytriphenylmethyl (DMT) protecting group on a primary hydroxyl function. After the DMT protecting group is removed an ODN can be built in step-wise fashion on this support, in accordance with steps known in the art, resulting in an ODN where the aromatic aldehyde moiety is attached to the 3' end. The ODN, still having the aromatic aldehyde at its 3' end is then removed from the solid support by methods well established in the state of the art.

Reaction Scheme 3 also discloses an exemplary synthetic route to provide a phosphoramidite reagent 10, where the aldehyde function is protected as the di-acetate. The phosphoramidite reagent 10 can be used in accordance with the state of the art for synthesizing ODNs where the aromatic aldehyde function is at the 5' end of the ODN. This reagent can also be used to incorporate the aldehyde function at internal position(s) in the ODN. It will be readily apparent to those skilled in the art based on the present disclosure that the linker between the CPG and the aromatic aldehyde can contain various combinations of C, N, O and S atoms or groups formed from these atoms.

The experimental section describes the conditions utilized for purification and deprotection of the diacetal and diacetate derivatives used in connection with this invention. The presence of an aldehyde group in the oligonucleotide that was synthesized utilizing the aldehyde containing support and/or the phosphoramidite reagent 10 can be confirmed with a reaction with 2,4-dinitrophenylhydrazine, followed by reversed phase HPLC analysis. This technique clearly distinguishes the resulting hydrazone-ODN from starting aldehyde-ODN. The aldehyde ODNs prepared in accordance with the present invention showed no noticeable change in reactivity when stored at −20° C. for months.

Coupling of the ODNs with the Modified Solid Support

The nucleophilic amino groups on the solid glass surface, as described above for the preferred embodiment, are reacted with the aldehyde groups attached to the 3'- or 5'- and of the ODN or to an internal base. Or alternatively, as described briefly above, the aromatic aldehyde is attached to the solid support (glass surface) and the amino group (preferably semicarbazide) is attached to the ODN.

Generally the coupling reactions are performed at pH's between 2 and 7, preferably at pH 6 and most preferably at pH 5. It has been found that, except for the pH the reaction conditions are not critical for the reaction. It was found, especially when semicarbazide $NH_2$ groups are used as in the preferred embodiment, that high concentrations of ODN per unit surface of the glass support can be achieved in accordance with the invention. Preferably concentrations of $10^4$ oligonucleotides/$\mu m^2$ and more preferably $10^5$ oligonucleotides/$\mu m^2$ are obtained in accordance with the invention. The semicarbazone linkage was determined to be stable at neutral and moderate basic pH's used in standard PCR and diagnostic assays.

Moreover, as another aspect or feature of the present invention an essentially background free solid support surface is achieved by treating the un-reacted $NH_2$ groups on the solid support with an anionic generating reagent.

Exemplary glass-oligonucleotide conjugate products formed from reaction of the nucleophilic amino group containing solid support with the aldehyde derivitized oligonucleotide are shown in Formula 8

Formula 8

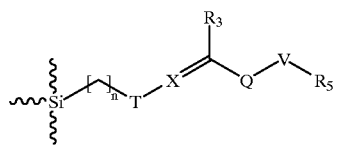

where n is 1 to 30; $R_3$ is H, $C_1$–$C_6$alkyl or $C_3$–$C_6$cycloalkyl; X is —N═; —UN═; —C═(U)—NH—N═; —NH—C═(U)—NH—N═; —NH—NH—CH═(U)—NH—N═ or —U—NH—C═(U)—NH—N═; where U is independently O or S; Q is an aromatic ring which may be carbocyclic and may be a condensed ring structure such as naphthalene, dihydro or tetrahydronaphthalene, or a heteroaromatic ring that may be 5 or 6 membered (e.g. thiophene or pyridine) or a heteroaromatic ring that is part of a condensed ring structure, such as quinoline, and where the ring itself may be substituted with substituents such as lower alkyl, lower alkoxy or halogen); V is a linker that can be 2 to 100 atoms long and may contain atoms selected from C, H, N, O and S and in addition may contain one or more of —NH—, —OH, —O—, —NH—C(═O)—, —C═(O)—NH—, —NH—C(═O)—NH—, —NH—C(═S)—NH—, —S—, OP(O)($O^-$)O— or —S—S— groups; $R_5$ is —O—P═(O)(—$U^-$)-3'-oligomer of nucleotides or —O—P═(O)(—$U^-$)-5'-oligomer of nucleotides where U is O or S. T represents a valence bond or a linker like V. T has a carbon atom adjacent to X.

An alternative exemplary preferred embodiment where an aldehyde modified solid support is coupled to an ODN containing a nucleophilic amino group at 3'-, 5'- or an suitable for attaching a protected aromatic aldehyde to said internal base is shown by Formula 9.

Formula 9

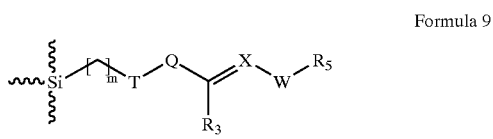

where m is 1 to 30; $R_3$ is H, $C_1$-$C_6$alkyl or $C_3$-$C_6$cycloalkyl; X is —N=; —UN=; —C=(U)—NH—N=; —NH—C=(U)—NH—N=; —NH—NH—CH=(U)—NH—N= or —U—NH—C=(U)—NH—N=; where U is independently O or S; Q is an aromatic ring which may be carbocyclic and may be a condensed ring structure such as naphthalene, dihydro or tetrahydronaphthalene, or a heteroaromatic ring that may be 5 or 6 membered (e.g. thiophene or pyridine) or a heteroaromatic ring that is part of a condensed ring structure, such as quinoline, and where the ring itself may be substituted with substituents such as lower alkyl, lower alkoxy or halogen); W is 2 to 100 atoms long and may contain atoms selected from C, H, N, O and S and in addition may contain one or more of —NH—, —OH, —O—, —NH—C(=O)—, —C=(O)—NH—, —NH—C(=O)—NH—, —NH—C(=S)—NH—, —S—, OP(O)(O$^-$)O— or —S—S— groups; R5 is —O—P=(O)(—U$^-$)-3'-oligomer of nucleotides or —O—P=(O)(—U$^-$)-5'-oligomer of nucleotides where U is O or S; T represents a valence bond or a linker like W. W and T have a carbon atom adjacent to X. Thus it should be understood that in Formulas 8 and 9 the groups V, W and T represent the possible linker groups attaching the Schiff base type bond to the solid support and to the ODN, as applicable.

Formula 10

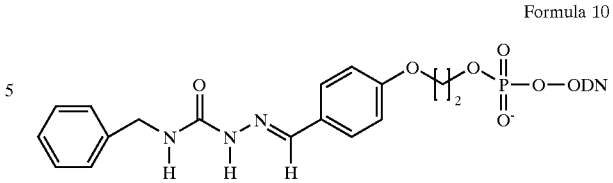

The semicarbazone conjugate (Formula 10) was treated in a PCR buffer at 95° C. for 30 minutes and analyzed by reversed phase HPLC chromatography. Comparison of the treated semicarbazone conjugate with the starting material showed little or no degradation.

Figure 6:
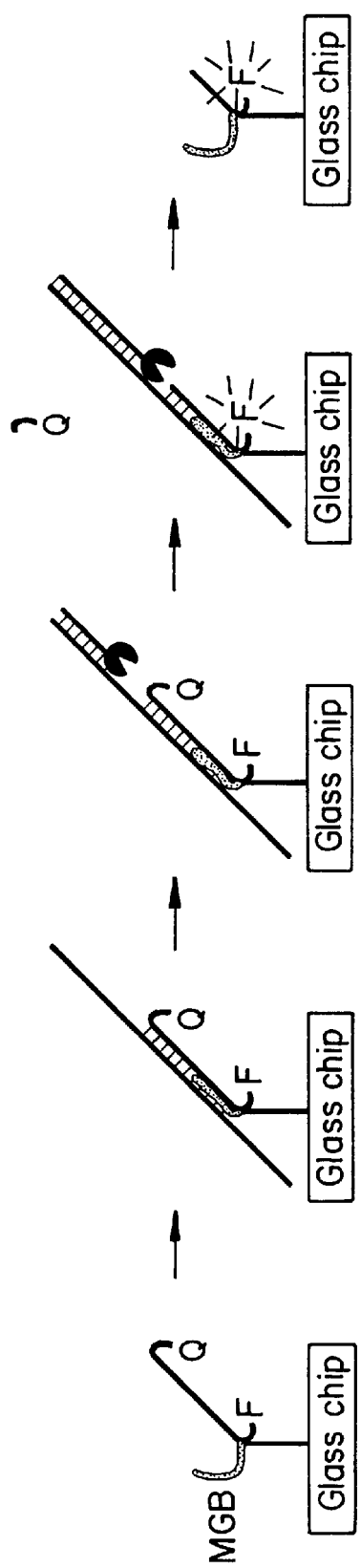
FIG. 6 is a schematic depiction of a solid support tethered 5' nuclease assay.

In another embodiment a solid surface linked oligonucleotides also contain appropriately held, minor grove binder, fluorescent generating moiety and a fluorescent quencher. This conjugate is designed such that during amplification reactions with a perfect complementary target the quencher molecules are cleaved during amplification by the 5'-nuclease activity, in analogy to the reaction described in U.S. Pat. No. 5,210,015 and in Witter al., Biotechniques 22: 130–138 (1997), resulting in a fluorescent immobilized oligonucleotide. Mismatched targets are not amplified and no fluorescent signal is generated. This is schematically in FIG. 6. The chemistries and methods to attach a minor groove binder (MGB), fluorophore (F) and quencher (Q) to an ODN has been described in U.S. Pat. No. 5,801,155, and in co-pending application Ser. No. 09/054,832, filed on Apr. 3, 1998, the specifications of which are incorporated herein by reference.

A CPG-CDPI3 with a 4 carbon linker blocked with a dimethoxytrytyl (DMTr) group as described by Luktanov et Reaction Scheme 4

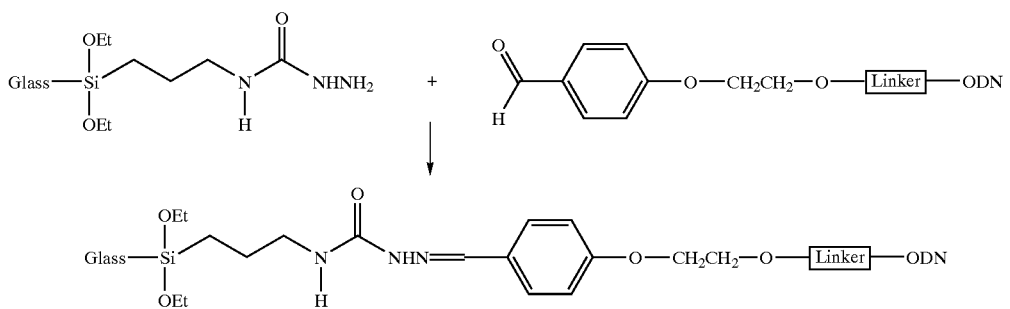

Reaction Scheme 4 discloses the formation of an ODN-to-glass conjugate linked with semicarbazone bonds in accordance with the presently most preferred embodiment of the invention.

In still other embodiments, the oligonucleotide is attached to the solid support through more than one type of aromatic aldehyde containing moiety introduced at either the 3', 5'or at internal nucleotides.

It is also within the scope of the present invention to immobilize a long chain DNA to a solid support that contains a semicarbazide moiety as disclosed above, with bisulfite catalyzed covalent attachment through cytidine residues, in analogy to the reaction described by Hayatsu in Biochem., 15: 2677–2682 (1976), incorporated herein by reference.

Stability of the semicarbazone linkage under PCR assay conditions were determined using a model compound shown below:

al., Bioconjug. Chem., 7: 564–567 (1996) incorporated herein by reference, can be deblocked under standard oligonucleotide synthesis conditions and reacted with aldehyde phosphoramidite in accordance with the invention. Deprotection of the DMTr group of this product allows the addition of a flourescein phosphoramidite (an available Glen Research Reagent). Normal oligonucleotide synthesis is performed on this product, including the addition of an aminohexyl tail in the last step. After standard deblocking the purified oligonucleotide is conjugated with carboxytetrametyl Rhodamine (TAMARA). The blocked aromatic aldehyde is now deprotected and reacted with the solid support to give the Fluorophore-MGB-ODN-Quencher conjugate shown in FIG. 6 of the appended drawings.

Materials for construction of arrays include, but are not limited to, nylon, polypropylene, nitrocellulose, glass, silicon wafers, optical fibers, copolymers and other materials suitable for construction of arrays such as are known to those of skill in the art.

Capping of Unreacted Groups on the Solid Surface

After the covalent attachment of the oligonucleotide the solid support via the semicarbazone linkage, the unreacted amino groups on the surface are treated with anion generating reagents aiding to limit non-specific primer and amplicon background. This is achieved by treatment of the solid surface with appropriate aromatic aldehydes (Formula 11). Similarly, when a semicarbazide-labeled oligonucleotide is coupled to aromatic aldehyde containing solid support, the unreacted aldehyde groups are reacted with anion generating reagents (Formula 12), where $R_6$ and $R_7$ are independently H—, —COO⁻, —OPO$_3^{2-}$ or —SO$_3^-$. Unreacted silanol groups can also be modified to further enhance surface characteristics. The appropriate silanes are commercially available (UCT, Bristol, Pa.).

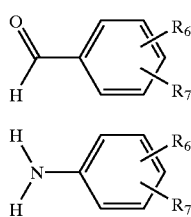

Formula 11

Formula 12

Hybridization Characteristics of Modified Solid Supports

The oligonucleotide loadings on the solid surface were determined by the use of 5'- or 3'-aldehyde-modified oligonucleotides $^{32}$P-labeled at opposing ends using the appropriate nucleotide triphosphate $^{32}$P-labeled and either terminal deoxynucleotidyl transferase or T4 polinucleotide kinase. The $^{32}$P-labeled oligonucleotide was reacted directly with the semicarbazide modified glass surface as small spots approximately 1.5 mm in diameter and the excess semicarbazide groups where capped by reaction with 4-formyl-1,3-benzenedisulfonic acid. Covalently bound oligonucleotide was quantified with a phosphor imager using a appropriate standard curve. Maximum attachment was achieved in about one hour at a surface density of about $10^5$ oligonucleotide molecules/$\mu$m$^2$. Reaction with oligonucleotide concentrations greater than 15 $\mu$M (>15 $\mu$M) yielded maximum immobilization on the glass surface.

The hybridization potential of the oligonucleotides immobilized via a semicarbazone linker to the solid support, was tested by direct capture of a complementary $^{32}$P-labeled oligonucleotide. Optimum capture of about 100 fmole oligonucleotide/spot could be achieved, when a concentration of about 275 fmole oligonucleotide/spot was applied to the solid surface. Additionally it was shown by phosphorimaging that a 235 bp amelogenine gene fragment PCR product separated into single strand, using a biotinylated primer and streptavidin beads, appropriately $^{32}$P-labeled, could be captured efficiently with the probe bound in accordance with the invention. In another demonstration six different captured oligonucleotides immobilized in an array each efficiently captured their complementary single stranded PCR amplified target.

Preferred Modes of Using the Invention

Oligonucleotide Arrays

In another embodiment of the present invention, immobilized oligonucleotides are used in procedures which utilize arrays of oligonucleotides, such as sequencing by hybridization and array-based analysis of gene expression. In sequencing by hybridization, an ordered array of oligonucleotides of different known sequences is used as a platform for hybridization to one or more test polynucleotides, nucleic acids or nucleic acid populations. Determination of the oligonucleotides which are hybridized and alignment of their known sequences allows reconstruction of the sequence of the test polynucleotide. Alternatively, oligonucleotides comprising the wild-type sequence and all possible mutant sequences for a given region of a gene of interest can be placed on an array. Exposure of the array to DNA or RNA from a subject or biological specimen, under hybridization conditions, allows determination of wild-type or mutant status for the gene of interest. This is described, without using the present invention, in the prior art, for example in U.S. Pat. Nos. 5,492,806; 5,525,464; 5,556,752; PCT publications WO 92/10588 and WO 96/17957, all of which are incorporated herein by reference. Both of the foregoing techniques require discrimination between related sequences, especially at the single-nucleotide level; hence, the simplicity, reproducibility of solid support attachment oligonucleotides of the invention provides improvements in these techniques. Materials for construction of arrays include, but are not limited to, nylon, polypropylene, nitrocellulose, glass, silicon wafers, optical fibers, copolymers and other materials suitable for construction of arrays such as are known to those of skill in the art.

An additional application of the present invention to array technology is in the examination of patterns of gene expression in a particular cell or tissue. In this situation oligonucleotides or polynucleotides corresponding to different genes are arrayed on a surface, and a nucleic acid sample from a particular cell or tissue type, for example, is incubated with the array under hybridization conditions. Detection of the sites on the array at which hybridization occurs allows one to determine which oligonucleotides have hybridized, and hence which genes are active in the particular cell or tissue from which the sample was derived.

Array methods can also be used for identification of mutations, where wild-type and mutant sequences are placed in an ordered array on a surface. Hybridization of a polynucleotide sample to the array under stringent conditions, and determination of which oligonucleotides in the array hybridize to the polynucleotide, allows determination of whether the polynucleotide possesses the wild-type or the mutant sequence. Since many mutant sequences of clinically-relevant genes differ from their wild-type counterpart at only one or a few nucleotide positions, the enhanced discriminatory powers of the modified oligonucleotides of the invention provides improvements in mutation detection.

Array methods can also be used in any diagnostic procedure where nucleic acid hybridization is feasible in combination with an appropriate detection system. The nucleic acids include DNA, RNA and sequences amplified by methods known in the art.

In all of the above-mentioned applications of array technology, the simplicity and efficiency of oligonucleotide attachment to solid supports in accordance with the invention provides significant improvements in manufacturing and performance of the arrays.

General

The availability of oligonucleotides containing an aldehyde linker directly from the oligonucleotide synthesizer allows the immobilization of oligonucleotides to any amine containing solid support. Thus oligonucleotide affinity chromatography material can be readily synthesized in accordance with the invention. In addition, the use of a primer labeled at the 3'-end with an aldehyde allows facile immobilization of the amplicon, after amplification, to an amine containing solid surface and allows the isolation of single strands after denaturation.

EXAMPLES

The following examples are included for illustrative purposes only and are not intended to limit the scope of the invention.

General Experimental

All air and water sensitive reactions were carried out under a slight positive pressure of argon. Anhydrous solvents were obtained from Aldrich (Milwaukee, Wis.). Flash chromatography was performed on 230–400 mesh silica gel. Melting points were determined on a Mel-Temp melting point, apparatus in open cappilary and are uncorrected. Elemental analysis was performed by Quantitative Technologies Inc. (Boundbrook, N.J.). UV-visible absorption spectra were recorded in the 200–400-nm range on a UV-2100 (Shimadzu) or a Lambda 2 (Perkin Elmer) spectrophotometers. $^1$H NMR spectra were run at 20° C. on a Bruker WP-200 or on a Varian XL-200 spectrophotometer; chemical shifts are reported in ppm downfield from $Me_4Si$. Thin-layer chromatography was run on silica gel 60 F-254 (EM Reagents) aluminum-backed plates.

Example 1

Preparation of (a,a-Dimethoxytolu-4-yl)-oxyethyl, 2-cyanoethyl N,N-diisopropylphosphoramidite (5)

4-Hydroxyethoxybenzaldehyde dimethyl acetal (3)

To a solution of 4-hydroxyethoxybenzaldehyde (Bernstein et al., J. Am. Chem. Soc., 73: 906–912 (1951); 8.5 g, 51.2 mmol), 2,2-dimethoxypropane (30 mL, 244 mmol) in a mixture of methanol (40 mL) and $CH_2Cl_2$ (100 mL) was added anhydrous Amberlyst 15 (Aldrich) (1.0 g). The mixture was stirred for 5 hrs, the catalyst was removed by filtration and the filtrate was concentrated to give the crude product contaminated with the starting aldehyde. This material was chromatographed on silica eluting with 1:1 ethyl acetate-hexane. The pure product fractions were pooled and concentrated. Drying under vacuum afforded 7.6 g (70%) of the title compound as a pale yellow, viscous liquid. $^1$H NMR: d 7.28 (d, J=9 Hz, 2H), 6.92 (d, J=9 Hz, 2H), 5.31 (s, 1H), 4.86 (t, J=5.5 Hz, 1H), 3.98 (t, J=5 Hz, 2H), 3.71 (q, J=5 Hz, 2H), 3.20 (s, 3H). $^{13}$C NMR: d 158.60, 130.19, 127.74, 113.90, 102.46, 69.43, 59.52, 52.27.

(a,a-Dimethoxytolu-4-yl)-oxyethyl, 2-cyanoethyl N,N-diisopropylphosphoramidite (5)

To a solution of 1 (4.76 g, 22.45 mmol) and ethyldiisopropylamine (10 mL) in 50 mL of anhydrous $CH_2Cl_2$ was added 2-cyanoethyl diisopropylchlorophosphoramidite (5.85 g, 24.7 mmol). After being stirred for 1 h, the reaction was treated with methanol (1 mL) to quench excess phosphitylating agent and diluted with $CH_2Cl_2$. The solution was washed with 5% sodium bicarbonate, brine and dried over $Na_2SO_4$. Concentration under vacuum gave an oil which was chromatographed on silica eluting with hexane-ethyl acetate-triethylamine (2:1:0.1). The desired product was obtained as a colorless, viscous syrup (6.3 g, 68%) after solvent evaporation and drying in vacuo.

Example 2

Preparation of Acetyloxy[4-(6-[bis(4-methoxyphenyl)phenylmethoxy]-5-{[bis(methylethyl)amino]-(2-cyanoethoxy)phosphinooxy}hexyloxy)phenyl]methyl acetate (10)

4-[4-(2,2-Dimethyl-1,3-dioxolan-4-yl)butoxy]benzaldehyde (6)

A solution of 4-hydroxybenzaldehdye (2.83 g, 23.22 mmol), toluene-4-sulfonic acid 4-(2,2-dimethyl-<1, 3>dioxolan-4-yl)-butyl ester (Lehmann et al., Carbohydr. Res., 169: 53–68 (1987); 7.62 g, 23.22 mmol) and 1,8-diazabicyclo[5,4.0]undec-7ene (3.6 ml) ml of anhydrous DMF was stirred at 85° C. for 4 h. The DMF was removed in vacuo and the residue was purified by silica gel chromatography eluting with 30% ethyl acetate in hexane. The pure product fractions were evaporated affording a homogenous oil: 4.93 g (75%) yield; TLC (1:1, ethyl acetate/hexane), $R_f$=0.68; $^1$H NMR (CDCl$_3$) 9.89 (1H, s, aldehyde), 7.83 (2H, d, J=8.9 Hz, aromatic), 6.98 (2H, d, J=8.8 Hz, aromatic), (2H, m, $CH_2$), 4.06 (2H, t, J=6.6 Hz, $CH_2$), 3.53 (1H, t, J=7.1 Hz, CH), 1.86 (2H, m, $CH_2$), 1.60(2H, m, $CH_2$), 1.41 and 1.36 (6H, 2×s, methyl). Anal. Calcd for $C_{16}H_{22}O_4$.0.15 $H_2O$: C, 68.38; H, 8.00. Found: C, 68.31; H, 8.08.

Acetyloxy{4-[4-(2,2-dimethyl(1,3-dioxolan-4-yl))butoxy]phenyl}methyl acetate (7)

Sulfuric acid (1.0 ml of a 1% solution in acetic anhydride) was added to a solution of 3 (4.78 g, 17.13 mmol) in 60 ml of acetic anhydride. The solution was stirred for 90 min at room temperature and then poured into 500 ml of ice-cold 5% sodium bicarbonate solution. The product was extracted into ethyl acetate (500 ml) and the extract was washed with water (2×500 ml), dried over sodium sulfate and evaporated affording 7 as an oil: 5.89 g (90%) yield; TLC (1:1, ethyl acetate/hexane), $R_f$=0.73; $^1$H NMR (CDCl$_3$) 7.62 (1H, s, acetal CH), 7.43 (2H, d, J=8.7 Hz, aromatic), 6.90 (2H, d, J=8.6 Hz, aromatic), 4.08 (2H, m, $CH_2$), 3.97 (2H, t, J=6.5 Hz, $CH_2$), 3.52 (1H, t, J=7.1 Hz, CH), 2.11 (6H, s, acetyl), 1.82 (2H, m, $CH_2$), 1.60 (2H, m $CH_2$), 1.41 and 1.36 (6H, 2×s, methyl). Anal. Calcd for $C_{20}H_{28}O_7$: C, 63.14; H, 7.42. Found: C, 63.19; H, 7.40.

Acetyloxy[4-(5,6-dihydroxyhexyloxy)phenyl]methyl acetate (8)

Trifluoroacetic acid (1.5 ml) was added to a solution of 7 (5.8 g, 15.26 mmol) in 20% aqueous methanol. The solution was stirred for 40 min at room temperature and then diluted with 400 ml of ethyl acetate and washed with 400 ml of 5% sodium bicarbonate solution followed by 400 ml of water. The organic solution was dried over sodium sulfate and evaporated. The residue was purified by silica gel chromatography eluting with a gradient of 50% hexane in ethyl acetate to 100% ethyl acetate to 5% methanol in ethyl acetate. The pure product fractions were evaporated affording an oil: 1.1 g (20%) yield; TLC (5% methanol in ethyl acetate), $R_f$=0.64; $^1$H NMR (CDCl$_3$) 7.62 (1H, s, acetal CH), 7.44 (2H, d, J=8.7 Hz, aromatic), 6.90 (2H, d, J=8.6 Hz, aromatic), 3.98 (2H, t, J=6.3 Hz, $CH_2$), 3.68 (1H, m, CH), 3.46 (2H, m, $CH_2$), 2.11 (6H, s, Acetyl), 1.82 (2H, m, $CH_2$), 1.55 (4H, m, $CH_2$). Anal. Calcd for $C_{17}H_{24}O_7$: C, 59.99; H, 7.11. Found: C, 60.26; H, 7.08

Acetyloxy(4-{6-[bis(4-methoxyphenyl)phenylmethoxy]-5-hydroxyhexyloxy}-phenyl)methyl acetate (9).

Dimethoxytrityl chloride (1.21 g, 3.57 mmol) was added to a solution of 8 (1.0 g, 2.94 mmol) in 17 ml of dry pyridine. The solution was stirred at room temperature for 2 h. and then poured into 250 ml of 5% sodium bicarbonate and extracted with 300 ml of ethyl acetate. The extract was dried over sodium sulfate and evaporated. The residue was purified by silica gel chromatography eluting with 50% hexane in ethyl acetate (1% triethylamine). The pure product fractions were pooled and evaporated affording a foam: 1.66 g (85%) yield; TLC (1:1, ethyl acetate/hexane), $R_f$=0.50; $^1$H NMR (CDCl$_3$) 7.62 (1H, s, acetal CH), 7.43 (2H, d, J=8.2 Hz, aromatic), 7.33–6.81 (17H, aromatic), 3.92 (2H, t, J=6.4 Hz, $CH_2$), 3.78 (6H, s, OCH$_3$), 3.17 (1H, dd, J=3.3 and 9.4

Hz, CH), 3.03 (1H, t, J=7.7 Hz, CH), 2.37 (1H, m, CH), 2.10 (6H, s, acetyl), 1.81–1.38 (6multiplets, CH$_2$). Anal. Calcd for C$_{38}$H$_{42}$O$_9$: C, 71.01; H, 6.59. Found: C, 70.91; H, 6.42. Acetyloxy[4-(6-[bis(4-methoxyphenyl)phenylmethoxy]-5-{[bis(methylethyl)amino]-(2-cyanoethoxy)phosphinooxy}hexyloxy)phenyl]methyl acetate (10)

2-Cyanoethyl diisopropylchlorophosphoramidite (0.49 ml, 2.19 mmol) was added to a solution of 9 (0.83 g, 1.29 mmol) dissolved in 32 ml of anhydrous methylene chloride containing 0.67 ml of N,N-diisopropylethylamine. The reaction solution was stirred for 1.0 h at 25° C. under argon and then treated with 1.0 ml of methanol and poured into 300 ml of 5% sodium bicarbonate solution. The mixture was extracted with ethyl acetate (300 ml) and the extract was dried over sodium sulfate and evaporated. The crude product was purified by silica gel chromatography eluting with a gradient of 25–50% ethyl acetate in hexane (2% triethylamine). The pure phosphoramidite fractions were evaporated affording a homogenous oil: 0.61 g (56%) yield; TLC (1:1, ethyl acetate/hexane), R$_f$=0.62; $^{31}$P NMR (DMSO-d$_6$) 147.82 (singlet). Anal. Calcd for C$_{47}$H$_{59}$N$_2$O$_{10}$P0.2 H$_2$O: C, 66.68; H, 7.07; N, 3.31. Found: C, 66.46; H, 7.27; N, 2.94.

Example 3

Preparation of CPG (12)

A solution of 9 (0.83 g. 1.29 mmol), succinic anhydride (0.15 g, 150 mmol), triethylamine (0.2 ml) and N-methyl imidazole (12 ul) in 3.0 ml of dry methylene chloride was stirred at room temperature under argon for 14 h. Pentafluorophenyl trifluoroacetate (0.39 ml, 2.32 mmol) was added and the solution was stirred for an additional 30 min. The reaction solution was loaded onto a silica gel column and eluted with 25% ethyl acetate in hexane (0.5% triethylamine included). The pure product fractions were pooled and evaporated affording a surup: 467-mg (40%) yield; TLC (1:1, ethyl acetate/hexane), R$_f$=0.56; $^1$H NMR (CDCl$_3$) 7.62 (1H, s, acetal CH), 7.42 (2H, d, J=8.3 Hz, aromatic), 7.33–6.72 (17H, aromatic), 5.16 (1H, t, J=5.8 Hz, CH), 3.90 (2H, t, J=6.0 Hz, CH$_2$), 3.77 (6H, s, methoxys), 3.16 (2H, m, CH$_2$), 3.01 (2H, t, J=6.4 Hz, succinyl CH$_2$), 2.80 (2H, t, J=6.5 Hz, succinyl CH$_2$), 2.11 (6H, s, acetyls), 1.82–1.32 (6H, multiplets, CH$_2$). Anal. Calcd for C$_{48}$H$_{45}$F$_5$O$_{12}$: C, 63.43; H, 4.99. Found: C, 63.65; H, 4.71.

Attachment of 11 to CPG (12)

To a suspension of controlled pore glass (LCAA 500 A, 4.2 g; loading, 283 umol/g) in 13.0 ml of anhydrous DMF was added 11 (226 mg, 0.252 mmol) and triethylamine (1.5 ml). The mixture was gently shaken under argon for 24 h. Anhydrous pyridine (84 ml) was then added followed by acetic anhydride (84 ml). The mixture was shaken for 1.0 h. The beads were filtered, rinsed with DMF and methanol and dried: loading—41 umol/g.

Example 4

Preparation of 3-(4-Semicarbazido) propyltriethoxysilane

Anhydrous hydrazine (3.2 ml; Aldrich, Milwaukee, Wis.) were dissolved in 30 ml of anhydrous acetonitrile. 2.5 g of isocyanatopropyltriethoxysilane (United Chemical Technologies, Bristol, Pa.) were added dropwise with vigorous stirring. Reaction mixture was stirred for 1 h at room temperature and the solvent was removed in vacuum. Oily residue was dissolved in anhydrous ethanol, the solution was filtered, and the solvent and unreacted hydrazine were evaporated under reduced pressure. The last step was repeated twice omitting filtration. The resulting viscous residue was dried in vacuum overnight to afford 2.7 g (yield 96%) of the desired product as a clear oil. $^1$H NMR: d 6.82 (s, 1H, NH), 6.32 (t, J=5.4 Hz, 1H, NH), 4.05 (br s, 2H, NH$_2$), 3.72 (q, J=7 Hz, 6H, CH$_2$), 2.96 (q, J=6.6 Hz, 2H, CH$_2$), 1.41 (m, 2H, CH$_2$), 1.26 (t, J=6.9 Hz, 9H, CH$_3$), 0.49 (m, 2H, CH$_2$).

Example 5

Oligonucleotide Synthesis

All oligonucleotides were synthesized on an ABI 392 DNA/RNA synthesizer using standard phosphoramidite chemistry. The dimethoxyacetal protecting group on the aldehyde was removed after HPLC by treatment with 80% acetic acid for 1 hour. The diacetyl protecting group on the aldehyde is removed at the treatment by ammonia step. The oligonucleotides were purified by reverse-phase HPLC, and their concentrations determined by UV spectrophotometry at 260 nm. Yield was similar to that observed in normal oligonucleotide synthesis.

Example 6

Derivatization of Glass Slides and Preparation of Oligonucleotide Arrays Preparation of Slides Glass slides were derivatized according to the standard silanization procedure described below. Pre-cleaned microscope slides (Corning Glass Works, Corning, N.Y.) were treated with 1N HNO$_3$ for 1 h at room temperature and then rinsed with running deionized water followed by anhydrous ethanol wash. The slides were then immersed in 1% 3-(4-semicarbazido)propyltriethoxysilane solution in 95% ethanol/water for 30 min. The slides were washed with 95% ethanol for 5 min, twice with acetonitrile, 5 min per wash, and finally with ether. After that the slides were cured for 45 min at 110° C. The derivatized slides can be stored at least for a month on a bench top in a dust proof container without noticeable loss of activity.

Immobilization of Oligonucleotides

Benzaldehyde-modified oligonucleotides were dissolved in 100 mM sodium acetate buffer (pH 5.0) at the desirable concentration and spotted manually directly on the derivatized slide as a 0.5 l droplets following a grid pattern on a wet paper template underneath the slide. Slides were incubated at 37° C. in a covered Petri dish located in a humid container for 1–5 hours. To block all unreacted semicarbazide groups on the glass surface the slides were treated with 100 mM solution of 4-formyl-1,3-benzenedisulfonic acid disodium salt in 100 mM sodium acetate buffer (pH 5.0) for 1 h at 37° C. The slides were then rinsed with water, washed for 30 min at 37° C. with 30% methanol in 0.5 M sodium phosphate buffer (pH 7.0) followed by a 30 min wash in 5'SSPE, 0.1% Triton X-100 at the same temperature. The slides were rinsed thoroughly with water, air dried at room temperature and were ready for use in hybridization experiments.

FIG. 1 shows the effect of different pH's and oligonucleotide concentration on immobilization efficiency. A pH of 5 and an oligonucleotide concentration of 20 mM showed optimum immobilization on glass surfaces.

Figure 2:
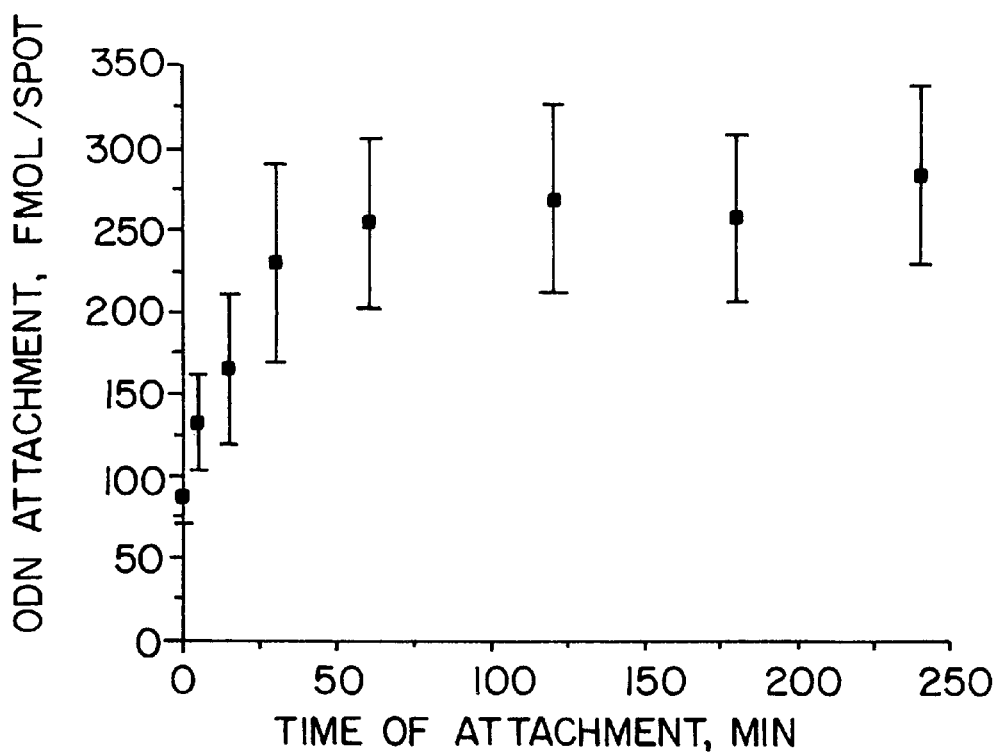
FIG. 2 is a graph showing the attachment of oligonucleotide to the glass surface as expressed in units of fmol/spot as a function of time.

FIG. 2 shows that optimum oligonucleotide immobilization is achieved on the glass surface in about 1 hour.

Example 7

Determination of Oligonucleotide Loading and Hybridization Efficiency

The 5' or 3' aldehyde-modified oligonucleotides were radioactively labeled at the opposite end using [a-$^{32}$P]ddATP (NEN, Boston, Md.) and terminal deoxynucleotidyl transferase (Promega, Madison, Wis.), or [g-$^{32}$P]ATP (Amersham, Arlington Heights, Ill.) and T4 polinucleotide kinase (NE Biolabs, Beverly, Mass.), respectively. Briefly, 1.2 nmol of oligonucleotide and 100 mCi of appropriate radioactive triphosphate were taken into a labeling reaction using the conditions specified by the manufacture. The labeled oligonucleotide was purified using NENSORBä 20 cartridge (NEN, Boston, Md.). Eluate from the cartridge containing labeled oligonucleotide was dried down, dissolved in 100 ml of 100 mM sodium acetate buffer (pH 5.0) and supplemented with 9 nmol of unlabeled oligonucleotide to approximately 100 mM final concentration. Serial dilution of this stock was made using the same buffer with a two fold decrement. 0.5 l of oligonucleotide solutions at various concentrations were applied in quadruplicates to semicarbazide-derivatized glass slide and allowed to react at 37° C for 3 h. The glass surface was blocked and washed as described above, and bound oligonucleotide was quantified by phosphor imaging using a Bio-Rad GS-250 Molecular Imager. The data from the phosphor imager were converted to fmol/spot by comparing to standard curves generated from a serial dilution of known amounts of the same labeled oligonucleotide probes spotted on a microscope slide and dried down without any washing.

To determine hybridization efficiency or availability of attached oligonucleotides for hybridization with a complementary target, an aldehyde-modified non-radiolabeled probe was immobilized on a slide as described above. 2.4'5.0 cm cover slip was positioned over the area where the probes were spotted using 0.2 mm thick spacers made from electric tape. 80–100 ml of hybridization mixture (1 mM 5' $^{32}$P-labeled complementary oligonucleotide, 5'SSPE, 0.1% Triton X-100) was applied by capillary action between the slide and the cover slip. The slide was incubated overnight at 37° C. in a closed Petri dish over wet Whatman 3MM paper in a humid container to prevent evaporation of the hybridization solution. Two 30 min washes were performed on a shaker with 25 ml per slide of hybridization buffer. The level of hybridization was quantified as described above.

Figure 3:
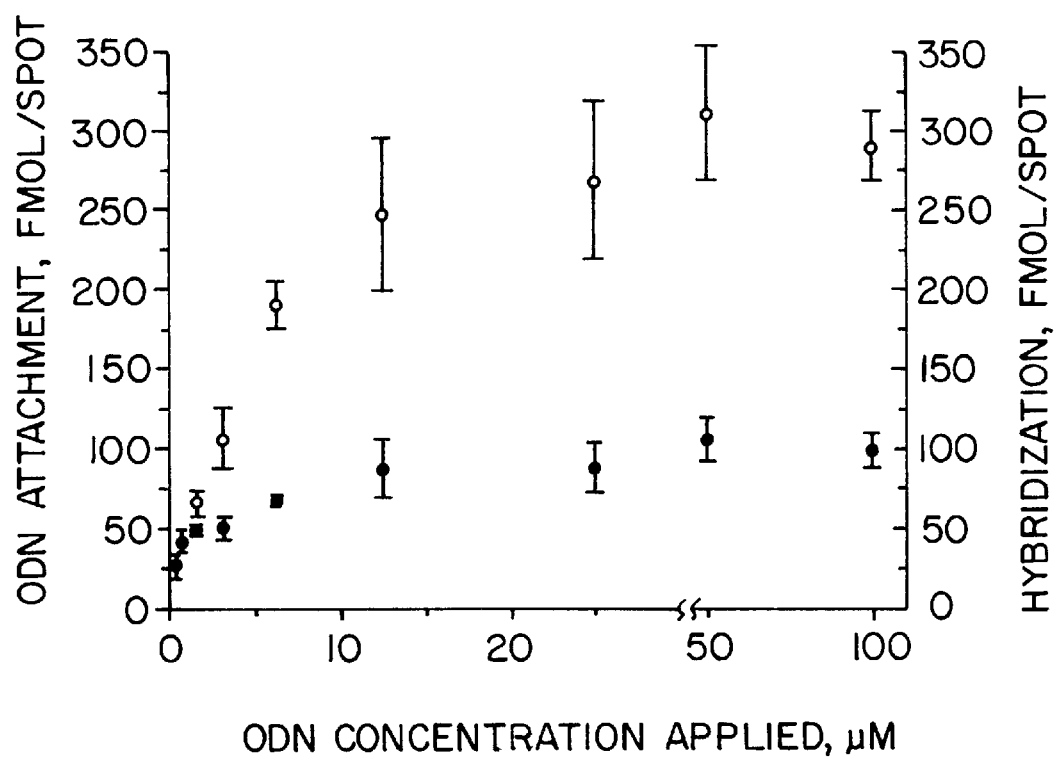
FIG. 3 is a graph showing the efficiency of oligonucleotide attachment and efficiency of hybridization as a function of oligonucleotide concentration applied on each spot.

FIG. 3 investigates the effect of oligonucleotide concentration applied in the immobilization reaction on the glass surface on covalent attachment and hybridization efficiencies. As shown, optimum hybridization target capture starts to occur at oligonucleotide applied concentrations of about 10 mM, that yields covalently attached oligonucleotide of >200 fmol/2 mm spot. Optimum oligonucleotide target capture of about 75–100 fmol/2 mm spot occurs.

Example 8

Hybridization of Oligonucleotide Arrays with Short Oligonucleotide Targets or Single-stranded PCR Products Female and male human genomic DNA samples were obtained from Coriell Institute of Medical Research (NIGMS Human Genetic Mutant Cell Repository, Camden, N.J.). The 235 bp amelogenine gene fragment corresponding to exon 3 was amplified by PCR using a set of primers, 5'-GCTGCACCACCAAATCATCCC-3' (SEQUENCE ID No. 15) and 5'-biotin-CTGGTGAGGCTGTGGCTGAAC-3' (SEQUENCE ID No. 16). The amplification reaction (100 ml) contained 50 mM KCl, 10 mM Tris-HCl (pH 8.3), 1.5 mM MgCl$_2$, 0.001% gelatin, 100 ng DNA, 1 mM of each primer, 200 mM each dATP, dCTP, dTTP and dGTP, and 2.5 units of JumpStartäTaq DNA polymerase (Sigma, St. Louis, Mo.). PCR was performed in a Statagene RoboCycler Gradient 40 Temperature Cycler (Stratagene, La Jolla, Calif.) using 35 cycles (95° C. for 1 min, 65° C. for 1 min, 72° C. for 1 min).

The PCR products were purified by 4% non-denaturing polyacrilamide gel electrophoresis. One DNA strand of PCR products derived from the non-biotinylated primer was 5' end labeled using [g-32P]ATP and T4 polynucleotide kinase. This labeled strand was separated using streptavidin-coupled magnetic beads Dynabeads M-280 (Dynal, Inc., Lake Success, N.Y.) according to manufacture's instructions. Briefly, 50 ml of labeling reaction mixture containing 1–2 mg of PCR product was diluted twice with 2'B&W buffer (10 mM Tris-HCl (pH 7.5), 1 mM EDTA, 2 M NaCl) and added to 1 mg of pre-washed Dynabeads. The suspension was incubated at room temperature for 15 min with occasional mixing. Beads were separated using the magnet, washed three times with 100 ml of B&W buffer and treated with 75 ml of 0.1 N NaOH to denature the DNA strands. The mixture was incubated at room temperature for 5 min, supernatant was collected, and denaturation step was repeated one more time. Combined supernatants were neutralized with equal volume of 0.1 N HCl and ethanol precipitated. The specificity of amplification was confirmed by sequencing the labeled strand using Maxam and Gilbert procedure (Maxam, A. M., & Gilbert, W. Proc. Natl. Acad. Sci. U.S.A. 79, 560–564(1977)).

Hybridization of oligonucleotide macroarrays consisting of six oligonucleotides spotted in triplicates with 5' labeled 30-mer complementary synthetic oligonucleotide targets was accomplished the same way as it had been described in the previous section, except for the hybridization time, which was reduced to 3 h. After that slides were washed for 15 min at room temperature in hybridization buffer (5'SSPE, 0.1% Triton X-100). Slides were then washed 2'15 min at 42° C. in 0.5'SSPE, 0.1% Triton X-100. In some cases an additional 15 min wash was necessary to improve the mismatch discrimination. Finally, the slides were air dried and analyzed by phosphorimaging.

To hybridize single stranded PCR product to the same array of oligonucleotides, the concentration of the target was 10–20 nM. Overnight hybridization at 37° C. was followed by 15 min wash in hybridization buffer, and 2'15 min wash at 37° C. in 0.5'SSPE, 0.1% Triton X-100.

Figure 4:
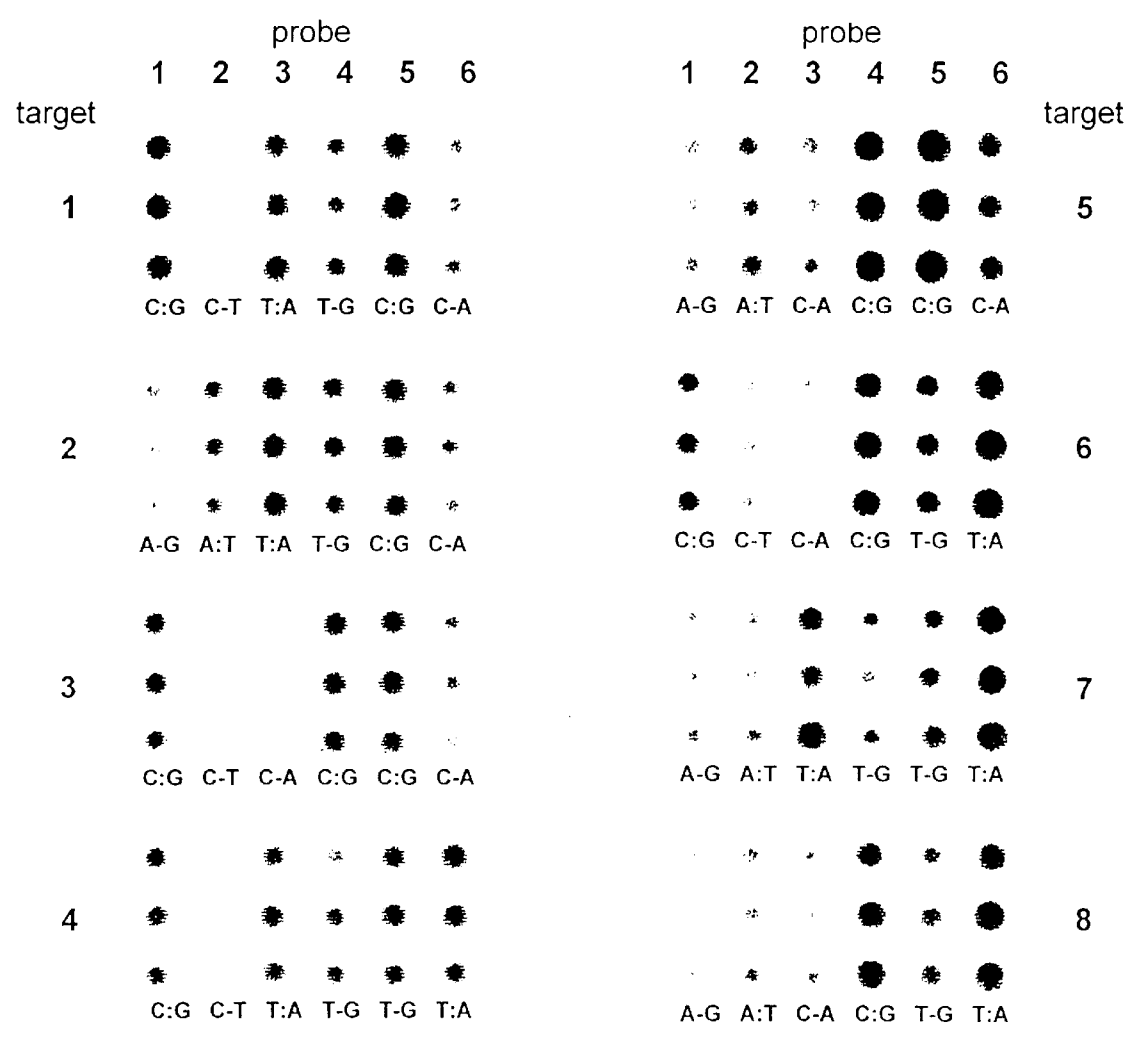
Figure 5:
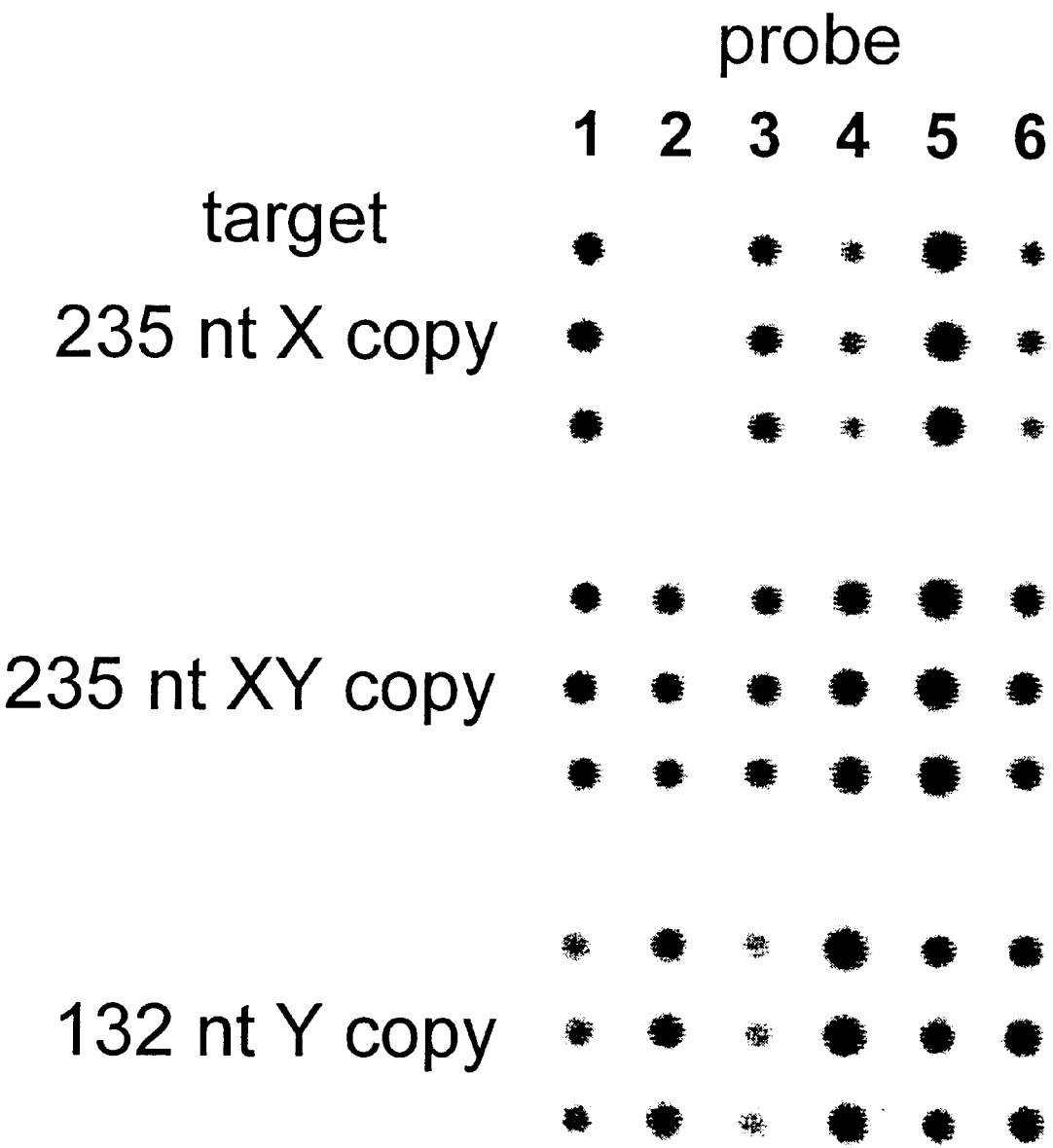
FIG. 5 is a depiction of a hybridization of the same macroarray of six ODN probes shown in FIG. 4 to single stranded 235-mer PCR products generated from female or male human genomic DNAs and to 132-mer product representing isolated male copy of amelogenin gene fragment, and wherein the PCR product generated from male DNA sample represents a heterozygous equimolar mixture of female and male copies of the gene fragment.

The oligonucleotide sequences of the primers and probes. used, are shown in Table 1. The specificity of the capture using an array of capture oligonucleotides is shown in FIGS. 4 and 5. Specifically, FIG. 4 is the depiction of a hybridization of macroarray consisting of six ODN probes to eight different 30-mer ODN targets, the sequences of which are disclosed in Table 1, wherein each oligonucleotide is spotted in triplicate giving an array of 3×6 spots and wherein the target sequences 1 and 8 correspond to X and Y copy of the amelogenin gene and wherein all other target sequences contain nucleotide substitutions at positions indicated in bold in Table 1 and wherein match or mismatch of the base pairs formed between each probe and the target are indicated at the bottom of each ODN triplicate. FIG. 5 is a depiction of a hybridization of the same macroarray of six ODN probes shown in FIG. 4 to single stranded 235-mer PCR products generated from female or male human genomic DNAs and to 132-mer product representing isolated male copy of amelogenin gene fragment, and wherein the PCR product generated from male DNA sample represents a heterozygous equimolar mixture of female and male copies of the gene fragment.

These results illustrate the reproducibility of the immobilization reactions. In addition the hybridization results show the expected results for the indicated match and mismatches.

TABLE 1

Sequences of Oliginucleotide Targets and Probes

| ODN name and SEQUENCE ID No. | Sequence | Type of mismatch (probe name in parenthesis) |
|---|---|---|
| [1]target 1 | 3'CAAACCGACCACCACAACCTAACCTCAGTACCTCAC 5' | C-T(2); T-G(4); C-A(6) |
| target 2 | 3'CAAACCGACCACCACAACCTAACCTCAGTACCTAAC 5' | A-G(1); T-G(4); C-A(6) |
| target 3 | 3'CAAACCGACCACCACAACCCAACCTCAGTACCTCAC 5' | C-T(2); C-A(3); C-A(6) |
| target 4 | 3'CAAACCGACTACCACAACCTAACCTCAGTACCTCAC 5' | C-T(2); T-G(4); T-G(4) |
| target 5 | 3'CAAACCGACCACCACAACCCAACCTCAGTACCTAAC 5' | A-G(1); C-A(3); C-A(6) |
| target 6 | 3'CAAACCGACTACCACAACCCAACCTCAGTACCTCAC 5' | C-T(2); C-A(3); T-G(5) |
| target 7 | 3'CAAACCGACTACCACAACCTAACCTCAGTACCTAAC 5' | A-G(1); T-G(4); T-G(5) |
| target 8 | 3'CAAACCGACTACCACAACCCAACCTCAGTACCTAAC 5' | A-G(1); C-A(3); T-G(5) |
| probe 1 SEQ. ID No. 9 | 5'Ald-TGGAGTCATGGAGTG 3' | |
| probe 2 SEQ. ID No. 10 | 5'Ald-TGGAGTCATGGATTG 3' | |
| probe 3 SEQ. ID No. 11 | 5'Ald-GTGTTGGATTGGAGT 3' | |
| probe 4 SEQ. ID No. 12 | 5'Ald-GTGTTGGGTTGGAGT 3' | |
| probe 5 ID No. 13 | 5'Ald-TTTGGCTGGTGGTG 3' | |
| probe 6 ID No. 14 | 5'Ald-TTTGGCTGATGGTG 3' | |

[1]Targets 1 through 8 represent ODNs having SEQUENCE ID Nos. 1–8 assigned to them, respectively.

5'Ald =

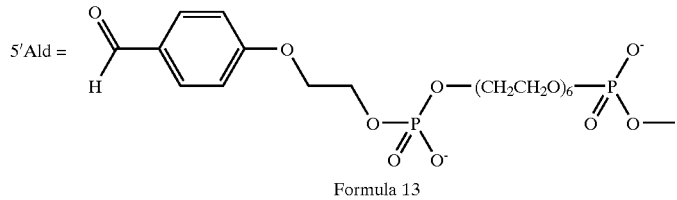

Formula 13

---

What is claimed is:

1. A derivatized solid support of formula (iii) or of formula (v):

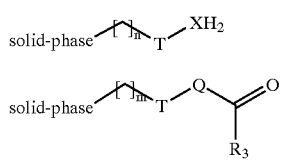

wherein
the subscript n is an integer of from 1 to 30;
the subscript m is an integer of from 1 to 30;
$R_3$ is a member selected from the group consisting of H, $C_1$–$C_6$alkyl and $C_3$–$C_6$cycloalkyl;
—$XH_2$ is a member selected from the group consisting of —NH—C=(U)—$NHNH_2$, —NH—NH—C=(U)—$NHNH_2$ and —U—NH—C=(U)—$NHNH_2$, wherein each U is independently selected from the group consisting of O and S;
Q is a member selected from the group consisting of substituted and unsubstituted carbocyclic aromatic rings and heteroaromatic rings;
when the derivatized solid support has the formula (iii), T is a valence bond or a linker having a length of 1 to 100 atoms, containing carbon to carbon bonds, and optionally carbon to oxygen bonds and optionally including one or more moieties selected from the group consisting of —NH—, —O—, —NH—C(=O)—, —C(=O)—NH—, —NH—C(=O)—NH—, —NH—C(=S)—NH—, —S— and —S—S—, —$XH_2$; and
when the derivatized solid support has the formula (v), T is a linker having a length of 1 to 100 atoms containing carbon to carbon bonds, and optionally carbon to oxygen bonds and optionally including one or more moieties selected from the group consisting of —NH—, —O—, —NH—C(=O)—, —C(=O)—NH—, —NH—C(=O)—NH—, —NH—C(=S)—NH—, —S— and —S—S—, with the proviso that said linker has a carbon atom adjacent to —$XH_2$.

2. A derivatized solid support of claim 1, having formula (iii).

3. A derivatized solid support of claim 2, wherein —$XH_2$ is selected from the group consisting of —C(=O)—$NHNH_2$ and —NH—C(=O)—$NHNH_2$.

4. A derivatized solid support of claim 1, wherein Q is a substituted or unsubstituted carbocyclic aromatic ring.

5. A derivatized solid support of claim 4, wherein Q is an unsubstituted carbocyclic aromatic ring.

6. A derivatized solid support of claim 5, wherein Q is an aromatic ring selected from the group consisting of benzene and naphthalene.

7. A derivatized solid support of claim 1, wherein Q is a substituted aromatic ring, and the substituents are selected from the group consisting of lower alkyl, lower alkoxy and halogen.

8. A derivatized solid support of claim 1, wherein Q is a substituted or unsubstituted heteroaromatic ring.

9. A derivatized solid support of claim 8, wherein Q is an unsubstituted heteroaromatic ring.

10. A derivatized solid support of claim 9, wherein Q is a heteroaromatic ring selected from the group consisting of thiophene, pyridine and quinoline.

11. A derivatized solid support of claim 8, wherein Q is a substituted heteroaromatic ring, and the substituents are selected from the group consisting of lower alkyl, lower alkoxy and halogen.

12. A derivatized solid support of claim 1, wherein the solid support is glass, nylon, polypropylene, nitrocellulose, silicon wafers, optical fibers, or a copolymer.

13. A derivatized controlled pore glass support of the formula:

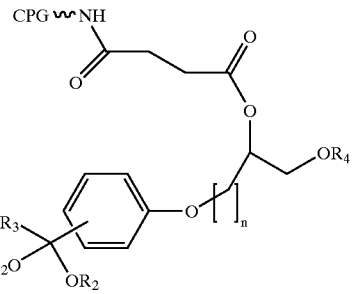

wherein
the subscript n is an integer of from 1 to 30;
$R_2$ is a member selected from the group consisting of $C_1$–$C_6$alkyl and $C_1$–$C_6$acyl, or optionally the two $R_2$ groups are combined to form a ring having from two to four carbon atoms in addition to the oxygen atoms bearing each of said $R_2$ groups;

$R_3$ is a member selected from the group consisting of H, $C_1$–$C_6$alkyl and $C_3$–$C_6$cycloalkyl; and $R_4$ is a member selected from the group consisting of H and dimethoxytriphenylmethyl.

14. A derivatized controlled pore glass support in accordance with claim 13, wherein $R_3$ is H.

15. A derivatized controlled pore glass support in accordance with claim 13, wherein $R_3$ is H; n is 4 and each $R_2$ is $CH_3C(=O)$—.

16. A derivatized controlled pore glass support in accordance with claim 13, wherein the phenyl ring is further substituted by a halo, lower alkyl or lower alkoxy group.

17. A derivatized solid support of claim 1, wherein T is a linker having a length of 2 to 100 atoms.

* * * * *

SEQUENCE LISTING

<160> NUMBER OF SEQ ID NOS: 16

<210> SEQ ID NO 1
<211> LENGTH: 36
<212> TYPE: DNA
<213> ORGANISM: Artificial Sequence
<220> FEATURE:
<223> OTHER INFORMATION: Description of Artificial Sequence: target 1

<400> SEQUENCE: 1
cactccatga ctccaatcca acaccaccag ccaaac          36

<210> SEQ ID NO 2
<211> LENGTH: 36
<212> TYPE: DNA
<213> ORGANISM: Artificial Sequence
<220> FEATURE:
<223> OTHER INFORMATION: Description of Artificial Sequence: target 2

<400> SEQUENCE: 2
caatccatga ctccaatcca acaccaccag ccaaac          36

<210> SEQ ID NO 3
<211> LENGTH: 36
<212> TYPE: DNA
<213> ORGANISM: Artificial Sequence
<220> FEATURE:
<223> OTHER INFORMATION: Description of Artificial Sequence: target 3

<400> SEQUENCE: 3
cactccatga ctccaaccca acaccaccag ccaaac          36

<210> SEQ ID NO 4
<211> LENGTH: 36

```
<212> TYPE: DNA
<213> ORGANISM: Artificial Sequence
<220> FEATURE:
<223> OTHER INFORMATION: Description of Artificial Sequence: target 4

<400> SEQUENCE: 4
cactccatga ctccaatcca acaccatcag ccaaac                        36

<210> SEQ ID NO 5
<211> LENGTH: 36
<212> TYPE: DNA
<213> ORGANISM: Artificial Sequence
<220> FEATURE:
<223> OTHER INFORMATION: Description of Artificial Sequence: target 5

<400> SEQUENCE: 5
caatccatga ctccaaccca acaccaccag ccaaac                        36

<210> SEQ ID NO 6
<211> LENGTH: 36
<212> TYPE: DNA
<213> ORGANISM: Artificial Sequence
<220> FEATURE:
<223> OTHER INFORMATION: Description of Artificial Sequence: target 6

<400> SEQUENCE: 6
cactccatga ctccaaccca acaccatcag ccaaac                        36

<210> SEQ ID NO 7
<211> LENGTH: 36
<212> TYPE: DNA
<213> ORGANISM: Artificial Sequence
<220> FEATURE:
<223> OTHER INFORMATION: Description of Artificial Sequence: target 7

<400> SEQUENCE: 7
caatccatga ctccaatcca acaccatcag ccaaac                        36

<210> SEQ ID NO 8
<211> LENGTH: 36
<212> TYPE: DNA
<213> ORGANISM: Artificial Sequence
<220> FEATURE:
<223> OTHER INFORMATION: Description of Artificial Sequence: target 8

<400> SEQUENCE: 8
caatccatga ctccaaccca acaccatcag ccaaac                        36

<210> SEQ ID NO 9
<211> LENGTH: 15
<212> TYPE: DNA
<213> ORGANISM: Artificial Sequence
<220> FEATURE:
<223> OTHER INFORMATION: Description of Artificial Sequence: probe 1
<221> NAME/KEY: modified_base
<222> LOCATION: (1)
<223> OTHER INFORMATION: n = t modified by 5' Ald

<400> SEQUENCE: 9
nggagtcatg gagtg                                               15

<210> SEQ ID NO 10
<211> LENGTH: 15
<212> TYPE: DNA
<213> ORGANISM: Artificial Sequence
<220> FEATURE:
<223> OTHER INFORMATION: Description of Artificial Sequence: probe 2
```

```
<221> NAME/KEY: modified_base
<222> LOCATION: (1)
<223> OTHER INFORMATION: n = t modified by 5' Ald

<400> SEQUENCE: 10
nggagtcatg gattg                                                    15

<210> SEQ ID NO 11
<211> LENGTH: 15
<212> TYPE: DNA
<213> ORGANISM: Artificial Sequence
<220> FEATURE:
<223> OTHER INFORMATION: Description of Artificial Sequence: probe 3
<221> NAME/KEY: modified_base
<222> LOCATION: (1)
<223> OTHER INFORMATION: n = g modified by 5' Ald

<400> SEQUENCE: 11
ntgttggatt ggagt                                                    15

<210> SEQ ID NO 12
<211> LENGTH: 15
<212> TYPE: DNA
<213> ORGANISM: Artificial Sequence
<220> FEATURE:
<223> OTHER INFORMATION: Description of Artificial Sequence: probe 4
<221> NAME/KEY: modified_base
<222> LOCATION: (1)
<223> OTHER INFORMATION: n = g modified by 5' Ald

<400> SEQUENCE: 12
ntgttgggtt ggagt                                                    15

<210> SEQ ID NO 13
<211> LENGTH: 14
<212> TYPE: DNA
<213> ORGANISM: Artificial Sequence
<220> FEATURE:
<223> OTHER INFORMATION: Description of Artificial Sequence: probe 5
<221> NAME/KEY: modified_base
<222> LOCATION: (1)
<223> OTHER INFORMATION: n = t modified by 5' Ald

<400> SEQUENCE: 13
nttggctggt ggtg                                                     14

<210> SEQ ID NO 14
<211> LENGTH: 14
<212> TYPE: DNA
<213> ORGANISM: Artificial Sequence
<220> FEATURE:
<223> OTHER INFORMATION: Description of Artificial Sequence: probe 6
<221> NAME/KEY: modified_base
<222> LOCATION: (1)
<223> OTHER INFORMATION: n = t modified by 5' Ald

<400> SEQUENCE: 14
nttggctgat ggtg                                                     14

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: PCR primer
      for amplification of 235 bp amelogenin gene fragment corresponding
      to exon 3

<400> SEQUENCE: 15
```

```
gctgcaccac caaatcatcc c                                              21

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: PCR primer
      for amplification of 235 bp amelogenin gene fragment corresponding
      to exon 3
<221> NAME/KEY: modified_base
<222> LOCATION: (1)
<223> OTHER INFORMATION: n = c modified by biotin

<400> SEQUENCE: 16
ntggtgaggc tgtggctgaa c                                              21
```